United States Patent [19]

Hochlowski et al.

[11] Patent Number: 5,192,748

[45] Date of Patent: Mar. 9, 1993

[54] ANTIBIOTICS UNPHENELFAMYCIN AND PHENELFAMYCINS A-D

[75] Inventors: Jill E. Hochlowski, Green Oaks; Mark H. Buytendorp, Cary; Randal H. Chen, Buffalo Grove; James B. McAlpine, Libertyville, all of Ill.; Robert J. Theriault, Kenosha, Wis.; Marianna Jackson, Waukegan; James P. Karwowski, Mundelein, both of Ill.

[73] Assignee: Abbott Laboratories, Abbott Park, Ill.

[21] Appl. No.: 740,827

[22] Filed: Aug. 5, 1991

Related U.S. Application Data

[63] Continuation-in-part of Ser. No. 160,614, Feb. 26, 1988, abandoned, which is a continuation-in-part of Ser. No. 104,902, Oct. 6, 1987, abandoned.

[51] Int. Cl.$^5$ .................. A61K 31/71; C07H 15/00
[52] U.S. Cl. .................. 514/25; 536/16.8; 536/17.2; 536/17.9; 536/53; 514/53; 435/74; 435/888
[58] Field of Search .................. 536/16.8, 17.2, 17.9, 536/53; 514/25, 53; 435/74, 888; 424/122

[56] References Cited

U.S. PATENT DOCUMENTS 4,704,276 11/1987 Kantor .................. 424/122
4,705,688 11/1987 Carter et al. .................. 424/122

Primary Examiner—Johnnie R. Brown
Assistant Examiner—Elli Peselev
Attorney, Agent, or Firm—Andreas M. Danckers

[57] ABSTRACT

New antibiotics, unphenelfamycin and phenelfamycins A-D, are produced by microorganisms belonging to the genus Streptomyces. The antibiotics have antibacterial activity against gram-positive and gram-negative anaerobic organisms and are effective in improving the feed efficiency and growth rate of livestock, including poultry.

12 Claims, 14 Drawing Sheets

ANTIBIOTICS UNPHENELFAMYCIN AND PHENELFAMYCINS A-D

This is a continuation-in-part of co-pending U.S. patent application Ser. No. 160,614, filed Feb. 26, 1988, now abandoned, which is a continuation-in-part of U.S. patent application Ser. No. 104,902, filed Oct. 6, 1987, now abandoned.

TECHNICAL FIELD

This invention relates to new antibiotics and a process for making them, as well as the use thereof in treating bacterial infections in human and other animal patients and in improving livestock growth rate and feed efficiency.

BACKGROUND AND DISCLOSURE OF THE INVENTION

A number of antibiotics in the prior art belonging to the elfamycin family have been isolated from microorganisms belonging to the genus Streptomyces. The elfamycin family includes mocimycin (kirromycin), 5,6 dihydromocimycin, efrotomycin, aurodox, henicomycin, kirrothricin, factumycin, azdimycin and L-681,217. These antibiotics exhibit activity against gram-positive bacteria.

Other antibiotics derived from Streptomyces species include compounds LL-E19020 alpha and beta, obtained from a subspecies of S. lydicus. These compounds are disclosed in U.S. Pat. No. 4,705,688, issued to Carter et al., and are reported to have antibacterial and growth promotant properties. Although no structural formulae are given for LL-E19020 alpha and beta, it is believed that these compounds are identical to phenelfamycins E and F, described herein.

The present invention encompasses the novel antibiotic agents phenelfamycins A-D and unphenelfamycin. These agents, and the related compounds phenelfamycins E and F, have the following structures:

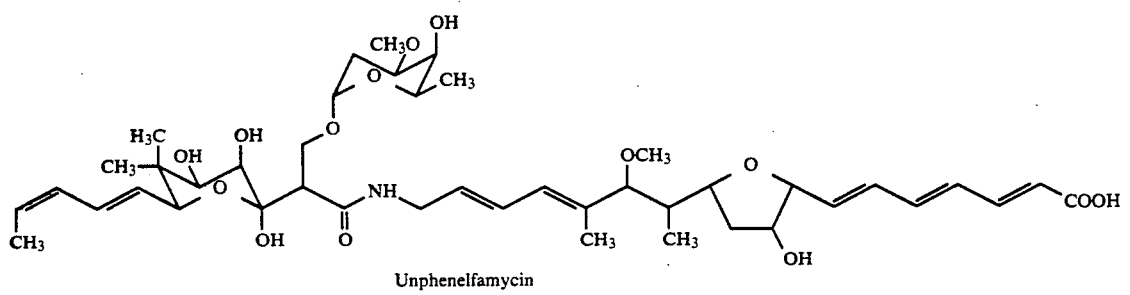
Unphenelfamycin

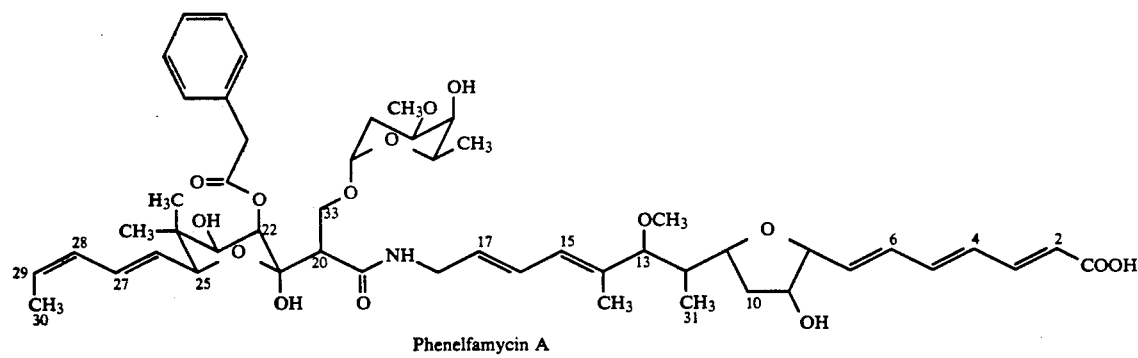
Phenelfamycin A

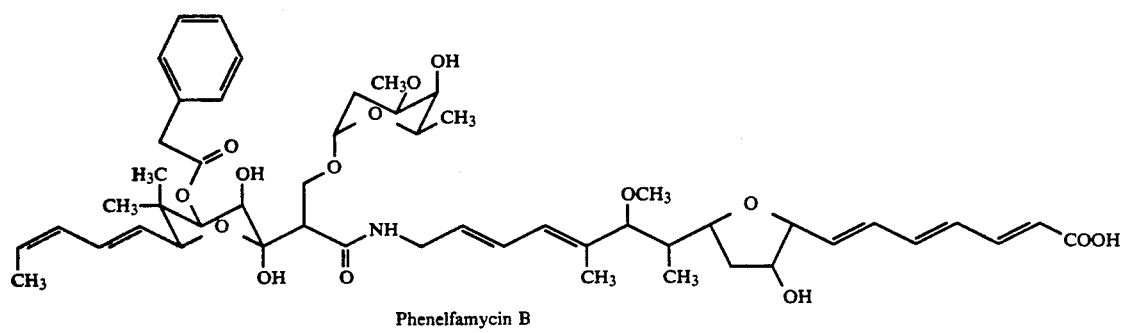
Phenelfamycin B

-continued

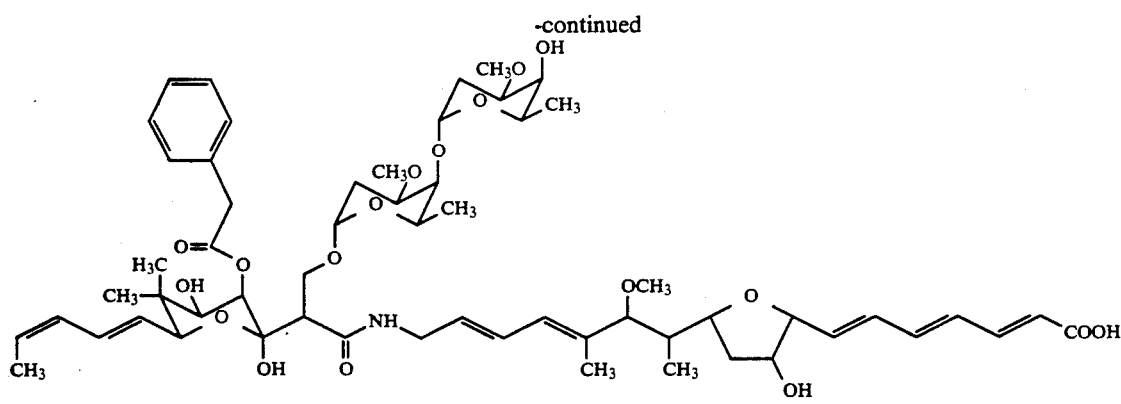
Phenelfamycin C

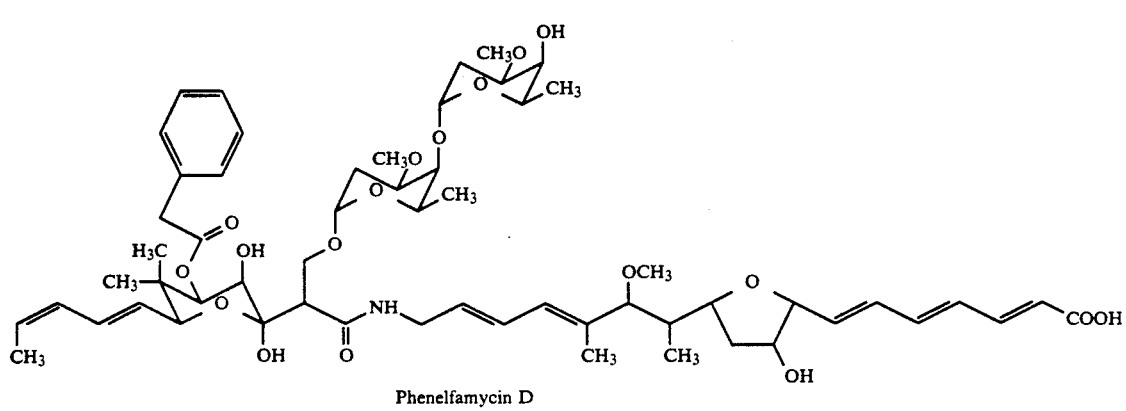
Phenelfamycin D

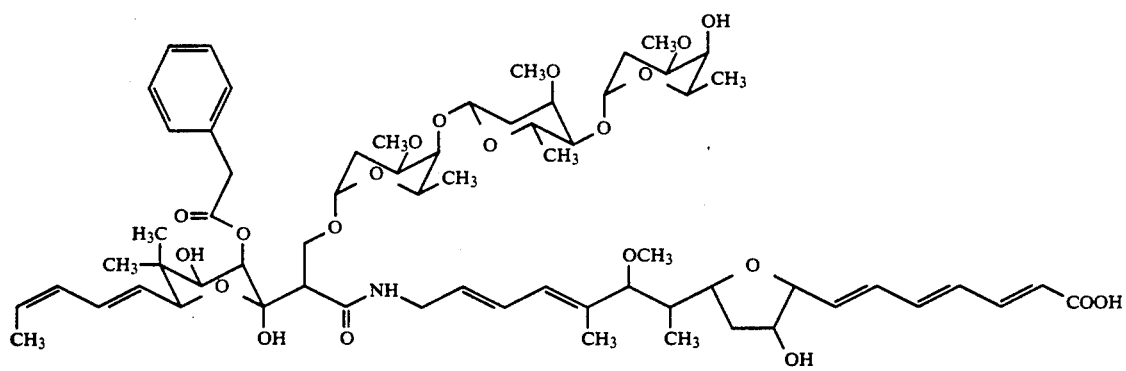
(unlabeled)

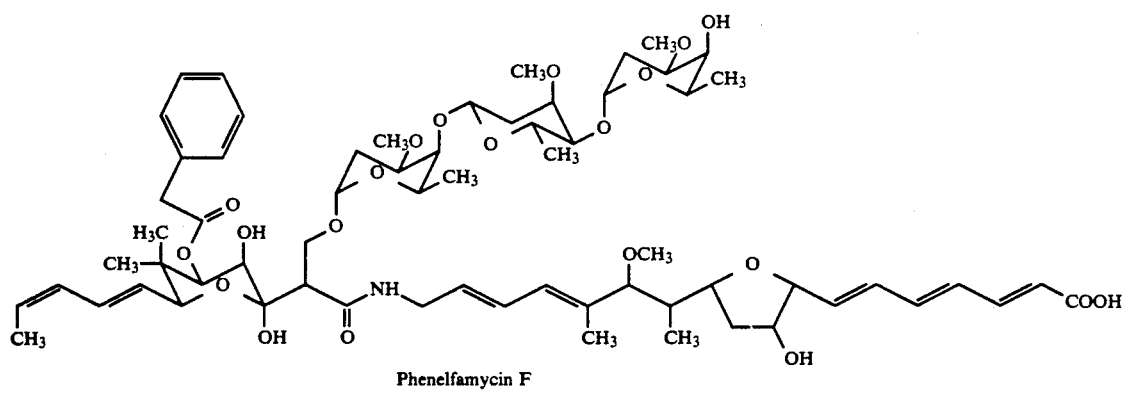
Phenelfamycin F

The phenelfamycins A–F and unphenelfamycin are produced by submerged aerobic fermentation of the microorganisms Streptomyces sp. AB-999F-80 and Streptomyces sp. AB-1047T-33. The compounds described exhibit antibiotic activity against a number of gram-positive and gram-negative anaerobic bacteria including strains of *Bacteroides fragilis, Veillonella parvula, Clostridium perfringens, C. difficile,* and *Propionibacterium acnes.* The antibiotics may be recovered from the fermentation broths of Streptomyces sp. AB-999F-

80 and Streptomyces sp. AB-1047T-33 by ethyl acetate extraction and from the mycelium by acetone steep.

DETAILED DESCRIPTION OF THE INVENTION

Figure 1:
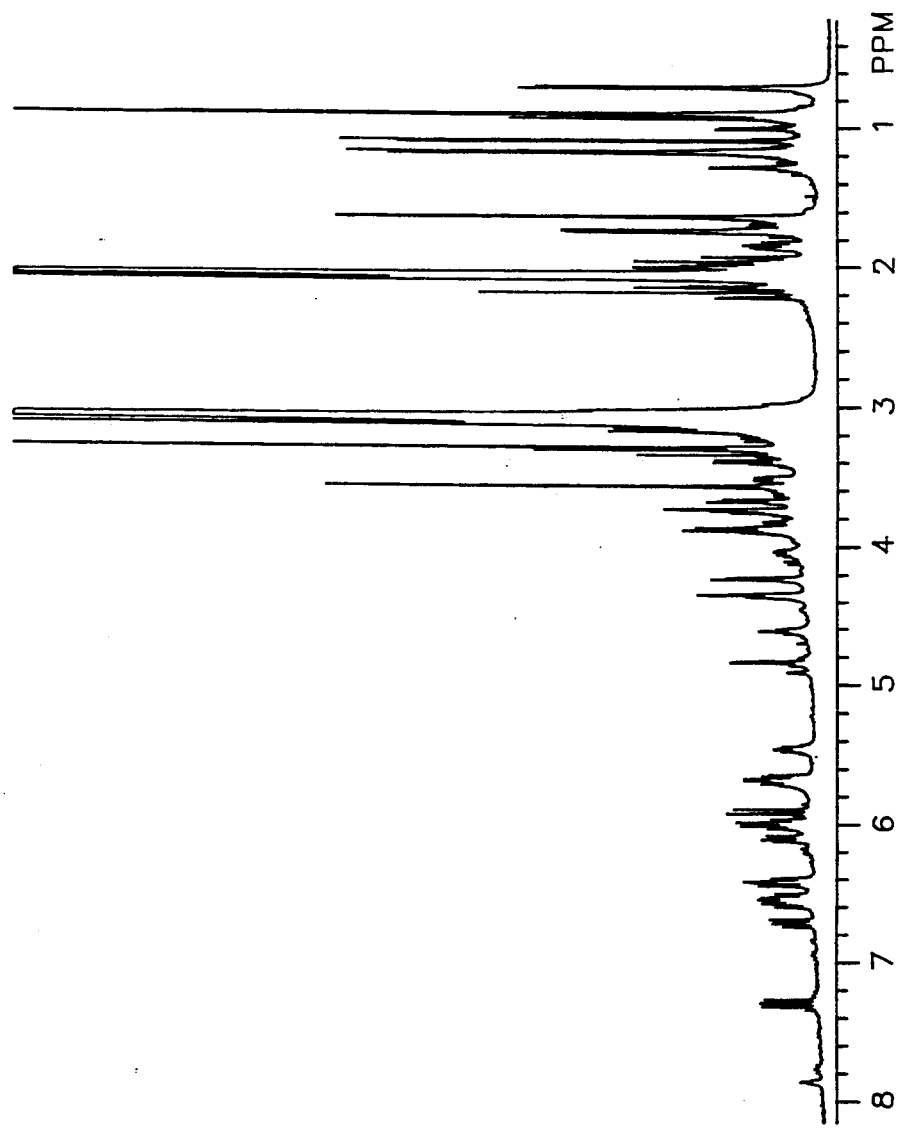
FIG. 1 is a hydrogen nuclear magnetic resonance spectrum of unphenelfamycin at 500 MHz in acetone $d_6$.

The microorganisms used in this invention to produce phenelfamycins A-F and unphenelfamycin are Streptomyces sp. AB-999F-80 and Streptomyces sp. AB-1047T-33. Subcultures of the microorganisms were deposited in the permanent collection of the Agricultural Research Service at Northern Regional Research Center, United States Department of Agriculture, 1815 North University Street, Peoria, Ill. 61604 U.S.A. The accession number at the depository for Streptomyces sp. AB-999F-80 is NRRL 18084 and NRRL 18290 for Streptomyces sp. AB-1047T-33 is NRRL 18290.

I. Morphology and Culture Characteristics

Streptomyces sp. AB-999F-80 was isolated from a soil collected at Mount Angel, Oreg. The color of aerial growth is white to gray. The appearance of this microorganism on eleven media is given in Table 1. The ability of the microorganism to grow on various carbon compounds in synthetic medium is shown in Table 2. Other growth and physiological characteristics are given in Table 3. Microscopic: Spores are borne in chains on aerial mycelium. The spore chains have a spiral morphology and their surface, when observed by scanning electron microscopy, is rugose. The average dimension of the spores is 0.64×0.67 microns.

Streptomyces sp. AB-1047T-33 was isolated from a soil collected at Niotaze, Kans. The color of aerial growth is white, yellow, or gray. The appearance of this microorganism on eleven media is given in Table 1A. The ability of the microorganism to grow on various carbon compounds in synthetic medium is shown in Table 2A. Other growth and physiological characteristics are given in Table 3A. Microscopic: Spores are borne in chains on aerial mycelium, and these spore chains have a spiral morphology.

Streptomyces sp. AB-999F-80 and Streptomyes sp. AB-1047T-33 are further characterized by production of phenelfamycins A-F and unphenelfamycin.

TABLE 1

Cultrual Characteristics of Streptomyces sp. AB-999F-80

| MEDIUM | CULTURAL | CHARACTERISTICS |
|---|---|---|
| Yeast extract-malt extract agar (ISP #2) | G: | *abundant |
| | AM: | sparse; white (263)** and medium gray (265) |
| | R: | light grayish yellowish brown (79) |
| | SP: | absent |
| Oatmeal agar (ISP #3) | G: | abundant |
| | AM: | brownish gray (64) |
| | R: | grayish yellow (90) |
| | SP: | absent |
| Inorganic salts-starch agar (ISP #4) | G: | moderate |
| | AM: | white (263) and medium gray (265) |
| | R: | light yellowish brown (76) |
| | SP: | absent |
| Glycerol-asparagine agar (ISP #5) | G: | moderate |
| | AM: | sparse; white (263) and light gray (264) |
| | R: | light yellowish brown (76) |
| | SP: | light grayish yellowish brown (79) |
| Peptone-yeast extract iron agar (ISP #6) | G: | poor |
| | AM: | absent |
| | R: | moderate; orange (53) |
| | SP: | absent |
| Tyrosine agar (ISP #7) | G: | abundant |
| | AM: | mottled; white (263) and brownish gray (64) |
| | R: | dark reddish brown (44) |
| | SP: | grayish brown (61) |
| Nutrient agar | G: | moderate |
| | AM: | absent |
| | R: | pale yellow (89) |
| | SP: | absent |
| Calcium malate agar | G: | moderate |
| | AM: | absent |
| | R: | grayish yellow (90) |
| | SP: | grayish yellow (90) calcium is dissolved |
| Czapek's agar | G: | moderate |
| | AM: | absent |
| | R: | yellowish white (92) |
| | SP: | absent |
| Gause #1 Modified soluble starch 0.1%, yeast extract 0.01%, KNO3 0.1%, K2HPO4 0.05%, MgSO4 0.05%, NaCl 0.05%, agar 2% | G: | poor |
| | AM: | brownish gray (64) |
| | R: | yellowish white (92) and brownish gray (64) |
| | SP: | absent |
| ATCC #172 | G: | moderate |
| | AM: | sparse; white (263) |
| | R: | light yellowish brown (76) to moderate orange (53) |
| | SP: | absent |

Observations after incubation for 21 days at 28° C.
*Abbreviations: G = growth; AM = aerial mycelium; R = reverse; SP = soluble pigment.
**Color and number in parenthesis follow the color standard in Kelly, K.L. & D.B. Judd: ISCC-NBS Color-Name Charts Illustrated with Centroid Colors. U.S. Dept. of Comm. Suppl. to Cri. 553, Washington, D.C. (1976).

TABLE 1A

Cultural Characteristics of Streptomyces sp. AB-1047T-33

| MEDIUM | CULTURAL | CHARACTERISTICS |
|---|---|---|
| Yeast extract-malt extract agar (ISP #2) | G: | *abundant, mottled |
| | AM: | medium gray (265)** with black coalescence (267) |

TABLE 1A-continued

Cultural Characteristics of Streptomyces sp. AB-1047T-33

| MEDIUM | CULTURAL | CHARACTERISTICS |
|---|---|---|
| | R: | strong yellowish brown (74) |
| | SP: | absent |
| Oatmeal agar | G: | moderate |
| (ISP #3) | AM: | light brownish gray (63) with black coalescence (267) |
| | R: | pale yellow (89) and medium gray (265) |
| | SP: | absent |
| Inorganic salts-starch agar | G: | moderate, mottled |
| (ISP #4) | AM: | light brownish gray (63) with black coalescence (267) |
| | R: | light grayish yellowish brown (79) and medium gray (265) |
| | SP: | absent |
| Glycerol-asparagine agar | G: | fair |
| (ISP #5) | AM: | moderate; white (263) |
| | R: | grayish yellow (90) |
| | SP: | absent |
| Peptone-yeast extract | G: | poor |
| iron agar | AM: | absent |
| (ISP #6) | R: | moderate orange (53) |
| | SP: | absent |
| Tyrosine agar | G: | moderate |
| (ISP #7) | AM: | grayish yellow (90) and dark grayish yellow (91) |
| | R: | deep yellowish brown (75) |
| | SP: | slight; grayish yellowish brown (80) |
| Nutrient agar | G: | poor, flat |
| | AM: | sparse; white (263) |
| | R: | grayish yellow (90) |
| | SP: | absent |
| Calcium malate agar | G: | fair |
| | AM: | grayish yellow (90) |
| | R: | grayish yellow (90) |
| | SP: | absent |
| | | calcium is dissolved |
| Czapek's agar | G: | moderate |
| | AM: | sparse; white (263) |
| | R: | light yellowish brown (76) |
| | SP: | absent |
| Gause #1 Modified | G: | moderate |
| soluble starch 0.1%, yeast | AM: | light brownish gray (63) with brownish black coalescence (65) |
| extract 0.01%, | | |
| $KNO_3$ 0.1%, | | |
| $K_2HPO_4$ 0.05%, | R: | medium gray (265) |
| $MgSO_4$ 0.05% | SP: | absent |
| NaCl 0.05%, agar 2% | | |
| ATCC #172 | G: | moderate |
| | AM: | sparse; white (263) |
| | R: | light yellowish brown (76) |
| | SP: | absent |

Observations after incubation for 21 days at 28° C.
*Abbreviations: G = growth; AM = aerial mycelium; R = reverse; SP = soluble pigment.
**Color and number in parenthesis follow the color standard in Kelly, K.L. & D.B. Judd: ISCC-NBS Color-Name Charts Illustrated with Centroid Colors. U.S. Dept. of Comm. Suppl. to Cri. 553, Washington, D.C. (1976).

TABLE 2

Utilization of Carbon Compounds* by Streptomyces sp. AB-999F-80

| Carbon Source | Growth |
|---|---|
| None | − |
| Glucose | ++ |
| Adonitol | ++ |
| Arabinose | ++ |
| Cellulose | − |
| Dulcitol | + |
| Fructose | ++ |
| Galactose | ++ |
| Inositol | ++ |
| Lactose | ++ |
| Mannitol | ++ |
| Melibiose | ++ |
| Raffinose | ++ |
| Rhamnose | ++ |
| Salicin | ++ |
| Sorbitol | ++ |
| Starch | + |
| Sucrose | ++ |
| Trehalose | ++ |
| Xylose | ++ |

Incubation at 28° C. for 21 days.
++ = Good utilization
+ = Poor utilization
− = Did no utilize
*Shirling, E.B. & D. Gottlieb: Methods for characterization of Streptomyces species. Intern. J. Syst. Bacteriol. 16:313-340, 1966.

TABLE 2A

Utilization of Carbon Compounds* by Streptomyces sp. AB-1047T-33

| Carbon Source | Growth |
|---|---|
| None | − |
| Glucose | ++ |
| Adonitol | ++ |
| Arabinose | ++ |
| Cellulose | − |
| Dulcitol | − |
| Fructose | ++ |
| Galactose | ++ |
| Inositol | ++ |
| Lactose | ++ |
| Mannose | ++ |
| Mannitol | ++ |
| Melezitose | − |
| Melibiose | ++ |
| Raffinose | ++ |
| Rhamnose | ++ |
| Salicin | ++ |
| Sorbitol | − |
| Starch | − |
| Sucrose | ++ |
| Trehalose | ++ |
| Xylose | ++ |

Incubation at 28° C. for 21 days.
++ = Good utilization
+ = Poor utilization
− = Did no utilize
*Shirling, E.B. & D. Gottlieb: Methods for characterization of Streptomyces species. Intern. J. Syst. Bacteriol. 16:313-340, 1966.

TABLE 3

Physiological Characteristics of Streptomyces sp. AB-999F-80

| Test | Reaction |
|---|---|
| Gelatin liquefaction | weak |
| Starch hydrolysis | + |
| Nitrate reduction | − |
| Melanin formation | − |
| $H_2S$ production | + |
| NaCl tolerance | 0~4% |
| Litmus milk | alkaline |
| Lysozyme resistance | − |
| Decomposition of: | |
| adenine | + |
| casein | + |
| L-tyrosine | + (weak) |
| xanthine | − |
| hypoxanthine | + |
| Antibiotic resistance | |
| erythromycin | + |
| neomycin | − |
| novobiocin | − |
| oxytetracycline | − |
| penicillin G | − |
| rifampicin | − |

TABLE 3-continued

Physiological Characteristics of Streptomyces sp. AB-999F-80

| Test | Reaction |
|---|---|
| streptomycin | – |
| vancomycin | – |
| Temperature range | Growth at ~15-37° C. optimum 28° C. |

TABLE 3A

Physiological Characteristics of Streptomyces sp. AB-1047T-33

| Test | Reaction |
|---|---|
| Starch hydrolysis | + |
| Nitrate reduction | + |
| Melanin formation | |
| H2S production | + |
| NaCl tolerance | 0-7% |
| Litmus milk | alkaline digestion |
| Decomposition of: | |
| adenine | + |
| casein | + |
| L-tyrosine | + (weak) |
| xanthine | – |
| hyposanthine | + |
| Temperature range | Growth at ~21-37° C. Optimum 32° C. |

II. Fermentation

Cultivation of Streptomyces sp. AB-999F-80 and Streptomyces sp. AB-1047T-33 for the production of phenelfamycin and unphenelfamycin is carried out in liquid media. An assimilable carbon source such as glucose is combined with an organic nitrogen source such as peptone plus whole yeast or yeast extract and inorganic salts. $CaCO_3$ is added to aid in controlling the pH of the fermentation. Other organic and inorganic ingredients may be added to stimulate production of the antibiotic.

A liquid, submerged, stirred culture process is preferred for the production of the antibiotic. Fermentations are carried out at a temperature range of 24° to 34° C. The pH of the fermentation is preferably maintained between 6 and 9. The antibiotic is produced and accumulated between 3 and 9 days after inoculation of the fermentation.

EXAMPLE 1

Streptomyces sp. AB-999F-80 was maintained on agar slants of a medium the ingredients of which are shown in Table 4. Medium S-4 seed tubes were inoculated from agar slant cultures of AB-999F-80 and incubated on a rotary shaker at 28° C. for 96 hours. (Shakers were set at 250 rpm, 3.2 cm stroke in all studies.) At that time, 5% vegetative inoculum from the first passage seed tubes was transferred aseptically to medium S-4 seed flasks (Table 4) which were also incubated on a rotary shaker at 28° C. for 72 hours. Five percent vegetative inoculum was then transferred to 200 fermentation flasks each containing 100 ml of a medium consisting of the following ingredients:

| Fermentation Medium N2B1 | gm/liter |
|---|---|
| Glucose monohydrate (added post-sterilization) | 20. |
| Molasses, BRER RABBIT brand, green label (Del Monte Corp., San Francisco, CA) | 5. |
| LEXEIN F-152 brand liquid peptone (made by Inolexl Chemical Co., Chicago, IL) | 10. |
| Yeast extract (available from Difco Laboratories, Detroit, MI) | 1. |
| $CaCO_3$ | 2. |
| Distilled water to 1.0 liter, no pH adjustment prior to sterilization | |

Volume/flask: 100 ml/500 ml Erlenmeyer flask closed with rayon plug

Sterilization: 30-35 min, 121° C., 15-16 psi

Fermentation flasks were incubated on a rotary shaker at 28° C. for 4 to 6 days. The fermentation broth was sampled, adjusted to pH 7, and then centrifuged at 1000 rpm for 30 min. The supernatant broth was decanted, concentrated, and then tested for antibiotic activity against a number of pathogenic bacteria in an agar diffusion inhibition zone test. The concentrated fermentation broth was found to inhibit *Bacteroides fragiles*, *Streptococcus pyogenes*, *Proteus vulgaris*, *Neisseria gonorrhoeae*, and *Candida albicans*.

EXAMPLE 1A

Streptomyces sp. AB-1047T-33 was maintained as frozen vegetative inoculum at −75° C. Medium 5B7 (Table 4) seed tubes were inoculated with 5% of the frozen vegetative cells of AB-1047T-33 from previous seed flasks and incubated on a rotary shaker at 28° C. for 96 hours. (Shakers were set at 250 rpm, 3.2 cm stroke in all studies.) At that time, 5% vegetative inoculum from the first passage seed tubes was transferred aseptically to medium S-4 seed flasks (Table 4) which were also incubated on a rotary shaker at 28° C. for 72 hours. Five percent vegetative inoculum was then transferred to 200 fermentation flasks each containing 100 ml of fermentation medium N2B1 (Example 1).

Volume/flask: 100 ml/500 ml Erlenmeyer flask closed with rayon plug

Sterilization: 30-35 min, 1210C, 15-16 psi

Fermentation flasks were incubated on a rotary shaker at 28° C. for 4 to 6 days. The fermentation broth was sampled, adjusted to pH 7, and then centrifuged at 1000 rpm for 30 min. The supernatant broth was decanted, concentrated, and then tested for antibiotic activity against a number of pathogenic bacteria in an agar diffusion inhibition zone test. The concentrated fermentation broth was found to inhibit *Bacteroides fragiles*, *Streptococcus pyogenes*, *Clostridium difficile*, and *Klebsiella pneumoniae*.

TABLE 4

Cultural Media Formulations

| | gm/liter |
|---|---|
| Agar Slant Medium (ATCC #5 modified) | |
| glucose | 10. |
| soluble starch | 20. |
| yeast extract | 1. |
| beef extract | 1. |
| tryptose | 2. |
| $FeSO_4.7H_2O$ | 0.002 |
| $CaCO_3$ | 1. |
| agar | 15. |
| Distilled water to 1.0 liter; pH adjusted to 7.0 to 7.2 prior to sterilization | |
| S-4 Seed Medium | |
| glucose monohydrate | 15. |
| soybean flour | 15. |

TABLE 4-continued

| Cultural Media Formulations | |
|---|---|
| | gm/liter |
| yeast extract (made by Difco Laboratories, Detroit, MI) | 1. |
| NaCl | 1. |
| CaCO$_3$ | 1. |
| Distilled water to 1.0 liter; no pH adjustment prior to sterilization. | |
| 5B7 Seed Medium | |
| glucose monohydrate | 10. |
| starch (Staclipse JUB) | 15. |
| yeast extract (Difco) | 5. |
| NZ amine type A (Sheffield) | 5. |
| CaCO$_3$ | 1. |
| Distilled water to 1.0 liter. Adjust pH to 7.0. | |

Volume/seed tube: 10 ml/25×150 mm glass tube closed with stainless steel cap
Volume/seed flask: 100 ml/500 ml Erlenmeyer flask closed with rayon plug
Sterilization: 30–35 min, 1210C, 15–16 psi

EXAMPLE 2

Medium S-4 seed tubes (Table 4) were inoculated from agar slant cultures of AB-999F-80. Seed tubes were incubated on a rotary shaker at 28° C. for 96 hours. Five percent inoculum from the first passage seed tubes was then transferred to medium S-4 seed flasks (Table 4) which were also incubated on a rotary shaker at 28° C. for 72 hours. Five percent vegetative inoculum from the second passage seed flasks was then used to inoculate a New Brunswick 150 liter fermentor. Medium and conditions were as follows:

| | |
|---|---|
| Fermentation medium: | N2B1 (see example 1) |
| Fermentor volume: | 80 liters |
| Fermentor antifoam agent: | .01% XFO-371 (Ivanhoe Chemical Co., Mundelein, IL) initially |
| Fermentor sterilization time: | 1.0 hour, 121° C., 15–16 psi |
| Fermentor incubation temp: | 28° C. |
| Fermentor aeration: | 0.7 vol/vol/min |
| Fermentor agitation: | 200 rpm |
| Fermentor head pressure: | 5 psi |

The fermentor was incubated for 5 days and then harvested. The concentrated supernatant fermentation broth was active against *Bacteroides fraglis* and *Clostridium difficile* in an agar diffusion inhibition zone test.

EXAMPLE 2A

Medium 5B7 seed tubes (Table 4) were inoculated with frozen vegetative inoculum of AB-1047T-33. Seed tubes were incubated on a rotary shaker at 28° C. for 96 hours. Five percent inoculum from the first passage seed tubes was then transferred to medium 5B7 seed flasks (Table 4) which were also incubated on a rotary shaker at 280C for 72 hours. Five percent vegetative inoculum from the second passage seed flasks was then used to inoculate a New Brunswick 150 liter fermentor. Medium and conditions were as follows:

| | |
|---|---|
| Fermentation medium: | N2B1 (see example 1) |
| Fermentor volume: | 80 liters |
| Fermentor antifoam agent: | DF-100S on demand |
| Fermentor sterilization time: | 1.0 hour, 121° C., 15–16 psi |
| Fermentor incubation temp: | 28° C. |
| Fermentor aeration: | 0.7 vol/vol/min |
| Fermentor agitation: | 200 rpm |
| Fermentor head pressure: | 5 psi |

The fermentor was incubated for 6 days and then harvested.

III. Isolation and Purification

Upon completion of fermentation the whole broth is adjusted to pH ca. 4–5 and filtered to remove the mycelial mass. Antibiotic is recovered from the filtered broth by repeated extraction with an organic solvent such as ethyl acetate, methylene chloride, methanol or the like. The extracts are combined and concentrated under reduced pressure to an oily residue. This residue is then subjected to further purification by partitioning between two-phase solvent systems, such as hexane/methanol or chloroform/methanol in aqueous acetate buffer (10 mM pH 5); by column chromatography (such as with a lipophilic size exclusion resin as for example SEPHADEX LH-20 brand resin) eluted with an appropriate organic solvent; or by diol partition chromatography. Antibiotic components are separated by either reverse phase chromatography on Baker C$_{18}$ bonded phase silica gel eluted with methanol/acetonitrile/water gradients or by countercurrent chromatography on an Ito multi-layer coil planet centrifuge. Antibiotic may also be recovered from the mycelial mass by lysing the cells with acetone, removing the acetone by filtration, and concentrating under reduced pressure. Purification of antibiotic obtained from mycelial steep is carried out similarly to that for material from the filtered broth extract.

EXAMPLE 3

Whole broth (80 liters) of Streptomyces sp. AB-999F-80 was adjusted to pH 4 with H$_2$SO$_4$ and filtered to remove the mycelial mass. The filtered broth was extracted with ethyl acetate (4×20 liters). Extracts were combined and concentrated under reduced pressure to leave an oily residue (10 g). The residue was partitioned between hexane and methanol (1:1) with activity remaining in the lower layer which was concentrated under reduced pressure to an oil. The oil was then partitioned between chloroform/methanol in aqueous acetate buffer (10 mM pH=5) with activity remaining in the lower layer which was concentrated to leave 8.4 g of residue. This residue was subjected to partition chromatography on diol-bonded silica gel eluted with the upper phase of a toluene/ethyl acetate/methanol/water (1:1:1:1) solvent system. Active fractions were combined and concentrated under reduced pressure to leave 2.5 g of an oily solid which was subjected to countercurrent chromatography in three batches on an Ito multi-layer coil planet centrifuge employing an ethyl acetate/toluene/methanol/water (1:1:1:1) solvent system. Active fractions from the three runs were combined and concentrated to leave 25 mg of solid material. This material was applied to a Baker C$_{18}$ bonded silica gel column and eluted with a gradient of water to methanol/acetonitrile (1:1) to yield pure phenelfamycin A (13 mg) and unphenelfamycin (12 mg).

EXAMPLE 4

Mycelial mass obtained from an 80 liter fermentation of Streptomyces sp. AB-999F-80 was steeped in acetone (5×1 liter) and the acetone extracts were combined and concentrated under reduced pressure to a residual oil (13 g). This residue was subjected to chromatography on a SEPHADEX LH-20 brand resin column eluted with methanol. Active fractions were combined and concentrated under reduced pressure to leave 3 g of an oily solid. This material was subjected to reverse-phase chromatography on Baker $C_{18}$ bonded silica gel eluted with a water through acetonitrile/methanol (1:1) solvent system to yield pure phenelfamycin A (300 mg).

EXAMPLE 5

Whole broth (20 liters) of Streptomyces sp. AB-999F-80 was adjusted to pH 4 with $H_2SO_4$ and filtered to remove the mycelial mass. The filtered broth was extracted with ethyl acetate (3×5 liters) and the extracts were combined and concentrated under reduced pressure to leave an oil (2.5 g). This oil was subjected to countercurrent chromatography on an Ito multi-layer coil planet centrifuge (CPC) employing a carbon tetrachloride/chloroform/methanol/water (2:1:4:1) solvent system. Active fractions from the CPC were combined and subjected to reversed-phase chromatography on a Baker $C_{18}$ bonded silica gel column eluted with a water/methanol gradient to yield pure phenelfamycin A (64 mg).

EXAMPLE 6

Whole broth (5100 liters) of Streptomyces sp. AB-999F-80 was desludged using a centrifugal solid/liquid/liquid separator (Model PX-207, De Laval, U.S.A.) then adjusted to pH 4.3 with concentrated $H_2SO_4$. Filtered broth was extracted with ethyl acetate (3×1500 liters). Extracts were combined and concentrated under reduced pressure to an dark oily residue. The residue was partitioned 3 times between methanol/hexane (60 liters of each), with the hexane layer being discarded and methanol retained each time. Combined methanol layers were concentrated under reduced pressure to an oily residue. The residue was partitioned between chloroform/methanol/aqueous 0.1% $H_2PO_4$, the upper layer discarded, and the lower layer retained. The lower layer was extracted with aqueous 0.05 M $NaHCO_3$ (4×10 liters). The bicarbonate extracts were combined and concentrated under reduced pressure to a residue. The residue was applied to a diol-bonded silica gel column eluted with both layers of a chloroform/ethyl acetate/methanol/water (3:3:2:4) solvent system. Active fractions from this column were combined and applied to a $C_{18}$-bonded phase silica gel column eluted with a gradient of 50 to 100% acetonitrile containing 0.1% acetic acid in water. Active fractions from this column were dissolved in approximately 10 liters of chloroform followed by 10 liters of heptane whereupon a precipitate formed. Mother liquors were chromatographed on a silica gel column eluted with a 10 to 15% isopropanol in methylene chloride gradient. Active fractions from the silica gel column were chromatographed on a LOBAR brand $C_{18}$ bonded phase column (E.M. Science, New Jersey) eluted with 50% acetonitrile/50% aqueous 0.1% $H_3PO_4$ to yield pure phenelfamycins A, B, C, D, E, and F. The heptane/chloroform precipitate fraction was chromatographed on SEPHADEX LH-20 brand resin and eluted with chloroform/heptane/ethanol (5:5:1) to yield pure phenelfamycins A, B, and C.

EXAMPLE 7

Whole broth (20 liters) of Streptomyces sp. AB-1047T-33 was adjusted to pH 7.0 with $H_2SO_4$, then centrifuged and filtered to remove the mycelial mass. Filtered broth was extracted with EtOAc (3×⅓ volumes), and the extracts were combined and concentrated under reduced pressure to a brown oil. This oil was applied to an XAD-2 brand polystyrene lipophilic non-specific affinity resin column (Rohm & Haas) and eluted with a 25 to 100% aqueous methanol gradient. Active fractions from this column were combined and concentrated under reduced pressure to a tan solid. This solid was applied to a Baker $C_{18}$ bonded phase column and eluted with $CH_3CN$-aqueous 0.1% acetic acid (1:1). Active fractions were combined into 2 pools based upon HPLC analysis of fractions to yield pure phenelfamycin E (15 mg/liter) and phenelfamycin F (9.6 mg/liter).

IV. Compounds of the Invention

Figure 8:
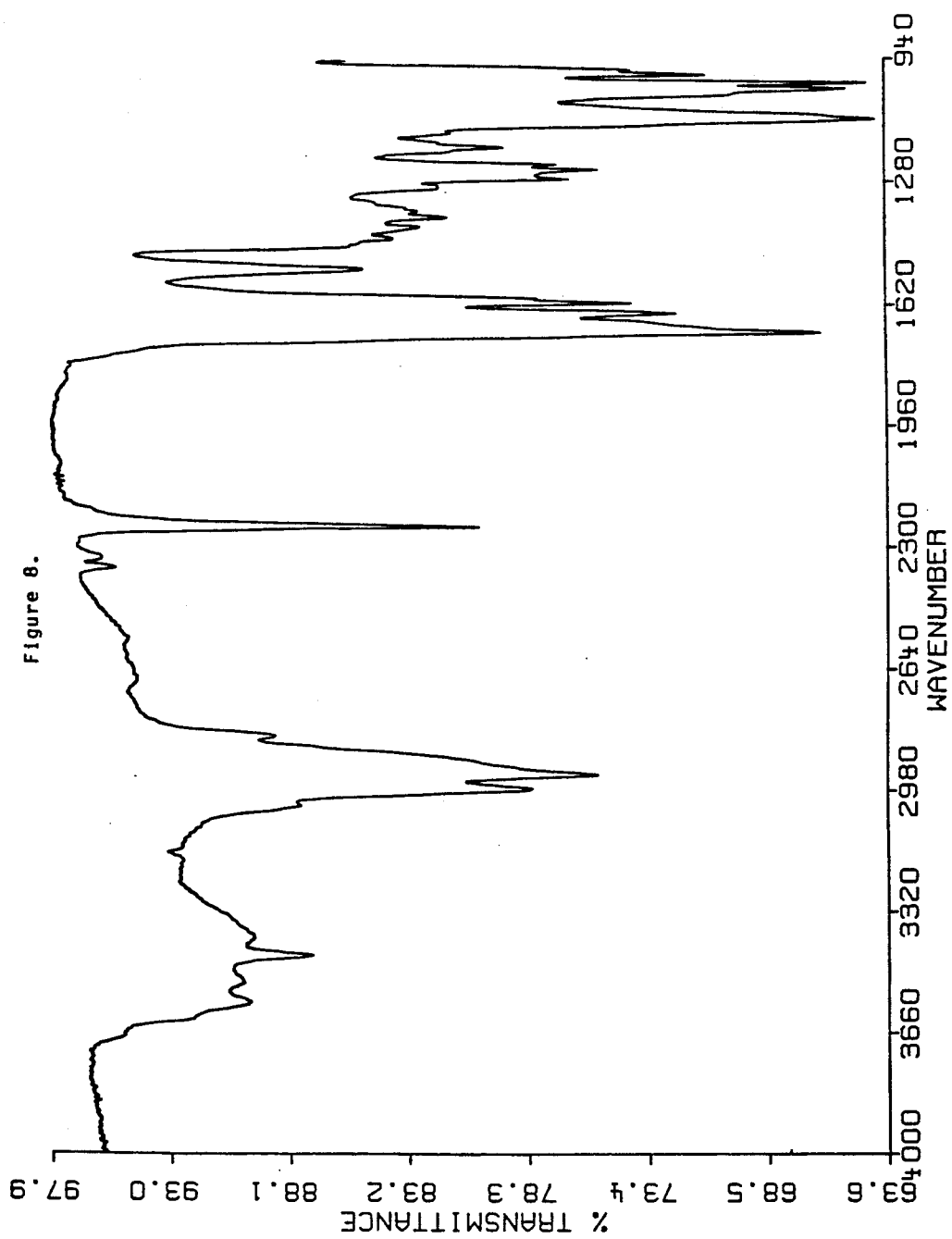
FIG. 8 is an infrared spectrum of unphenelfamycin in $CDCl_3$.

Unphenelfamycin, $[\alpha]_D^{25} = -17.0°$ (c=0.56, MeOH) is a light tan oil, readily soluble in acetone, acetonitrile, and dimethylsulfoxide, moderately soluble in chloroform and methylene chloride, and insoluble in hexane or water. A molecular weight of 841 was established for the sodium salt of unphenelfamycin by FAB positive ion mass spectrometry. An infrared spectrum measured in $CDCl_3$ (FIG. 8) contained bands at 3435, 2975, 2936, 1701, 1646, 1618, 1605, 1385, 1295, 1276, 1250, 1236, 1187, 1147, 1106, 1022, 1007, 985, and 974 $cm^{-1}$. The 500 MHz nuclear magnetic resonance spectrum shown in FIG. 1 and the infrared data are consistent with the assigned structure. The molecular formula is $C_{43}H_{65}NO_{14}$.

Figure 2:
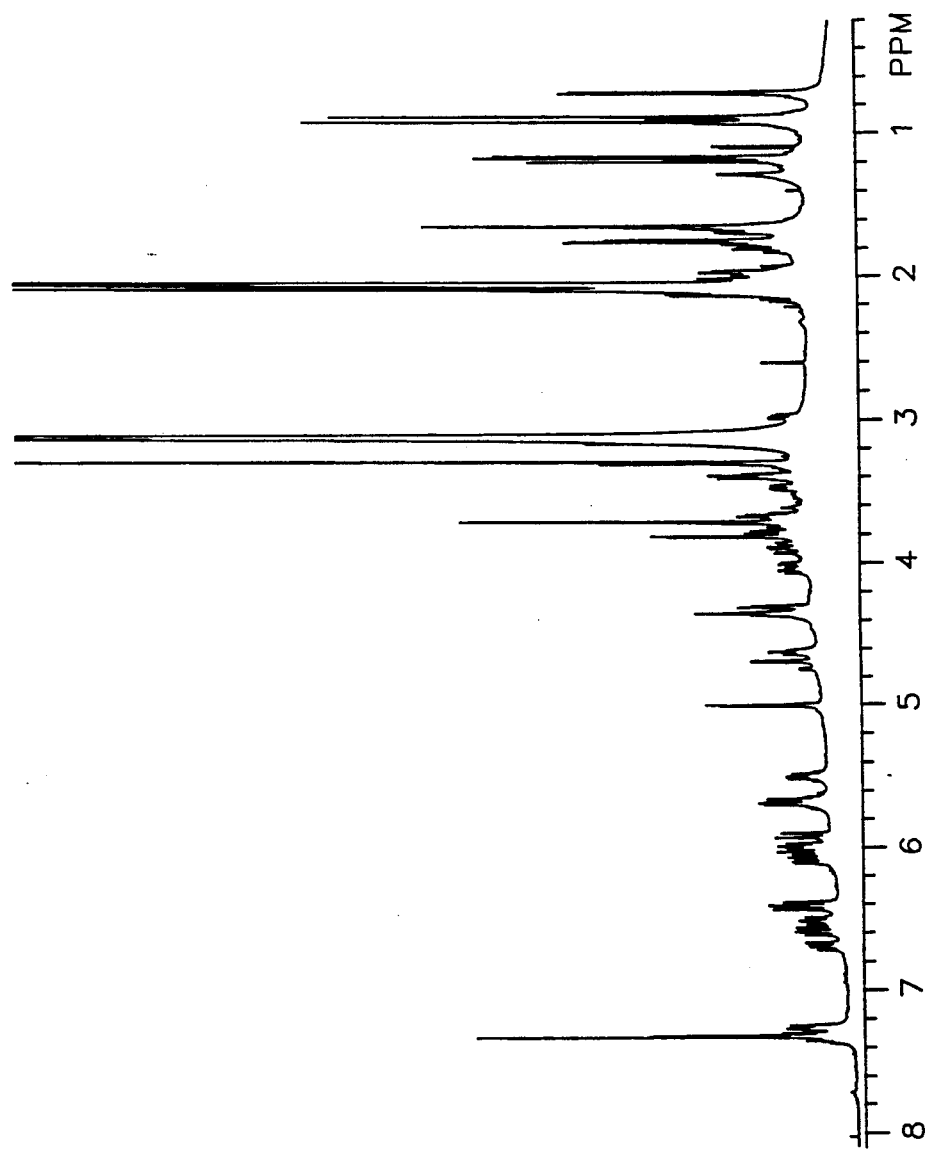
FIG. 2 is a hydrogen nuclear magnetic resonance spectrum of phenelfamycin A at 500 MHz in acetone $d_6$.
Figure 9:
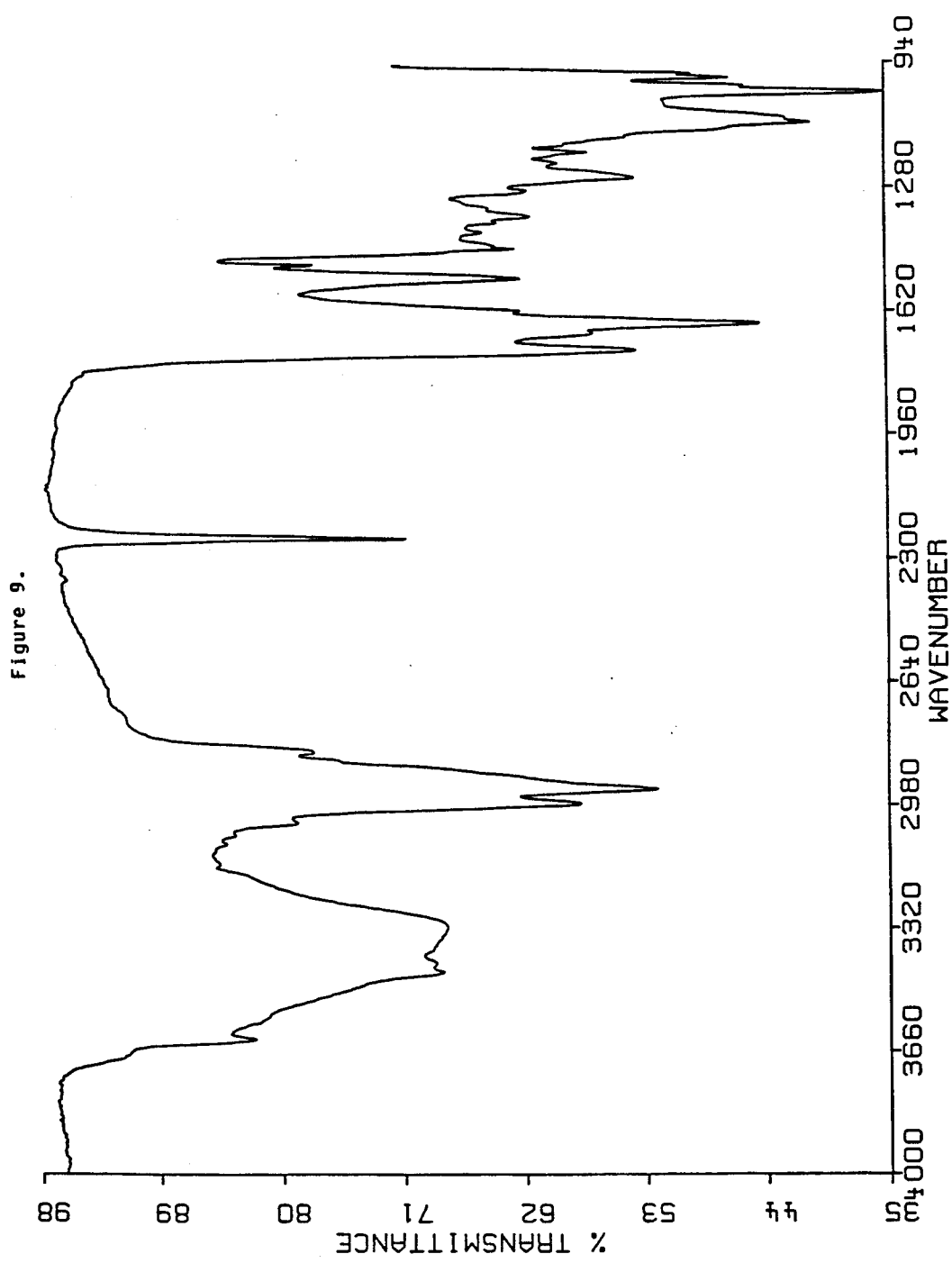
FIG. 9 is an infrared spectrum of phenelfamycin A in $CDCl_3$.

Phenelfamycin A, $[\alpha]_D^{25} -8.6°$ (c=0.1, MeOH), is a light tan powder with m.p. approximately 140° C. dec. Phenelfamycin A is readily soluble in acetone, acetonitrile, methanol, and dimethyl sulfoxide, moderately soluble in chloroform or methylene chloride, and insoluble in hexane or water. A molecular weight of 959 was established for the sodium salt of phenelfamycin A by FAB positive ion spectrometry. An infrared spectrum measured in $CDCl_3$ (FIG. 9) contained bands at 3443, 3370, 3320, 2978, 2938, 1730, 1683, 1655, 1622, 1533, 1446, 1411, 1384, 1365, 1343, 1295, 1257, 1217, 1188, 1145, 1105, 1022, 1005, 985, and 974 cm . The 500 MHz nuclear magnetic resonance spectrum shown in FIG. 2 and the infrared data are consistent with the assigned structure. The molecular formula is $C_{51}H_{71}NO_{15}$.

Figure 3:
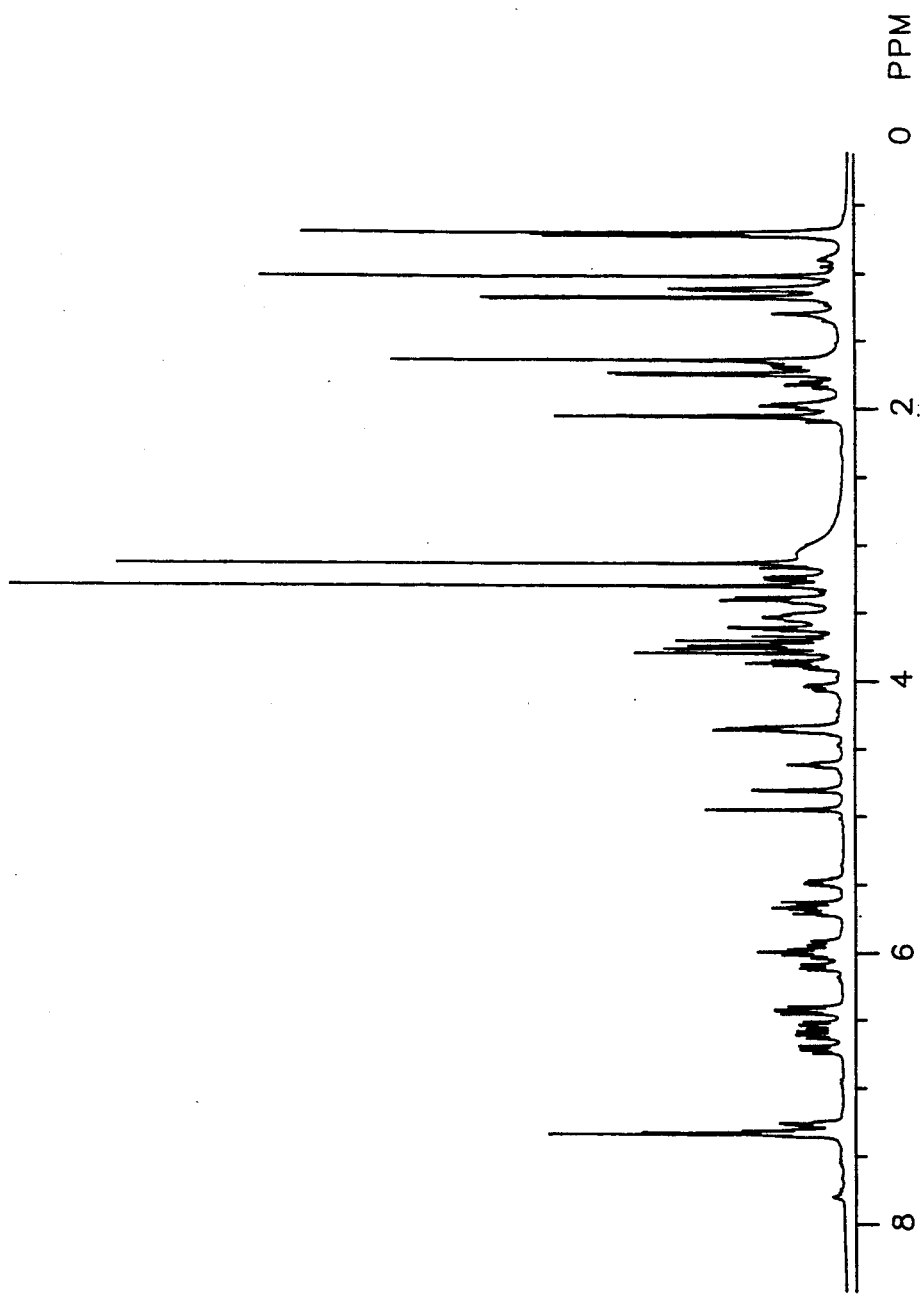
FIG. 3 is a hydrogen nuclear magnetic resonance spectrum of phenelfamycin B at 500 MHz in acetone $d_6$.
Figure 10:
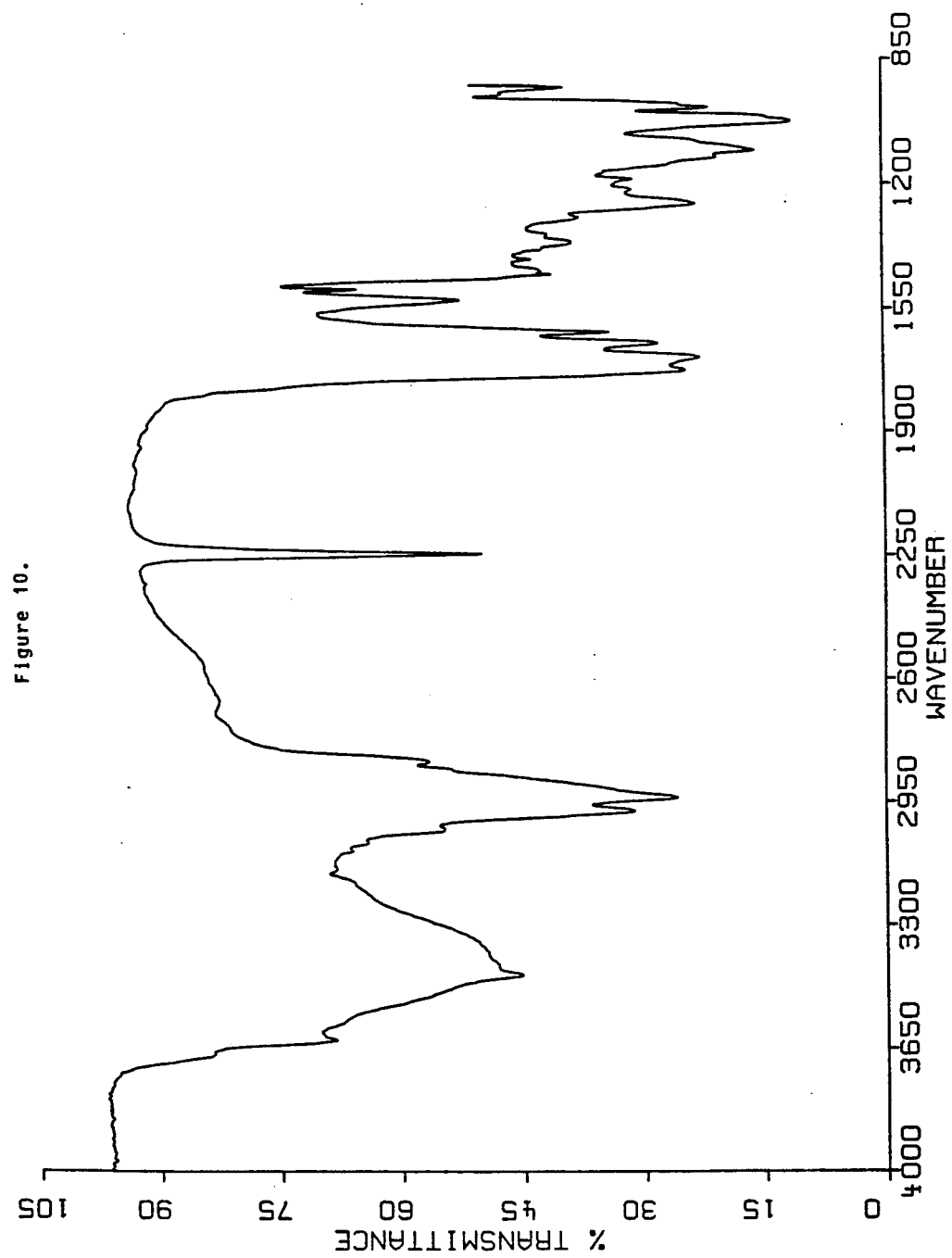
FIG. 10 is an infrared spectrum of phenelfamycin B in $CDCl_3$.

Phenelfamycin B, $[\alpha]_D^{25} = -10.0°$ (c=1.12, MeOH) is a light tan powder with m.p.=118° C. dec. Phenelfamycin B is readily soluble in acetone, methanol, or dimethyl sulfoxide, moderately soluble in chloroform and insoluble in hexane or water. A molecular weight of 959 was established for the sodium salt of phenelfamycin B by FAB positive ion mass spectrometry. An infrared spectrum measured in $CDCl_3$ (FIG. 10) contained bands at 3445, 3420, 2892, 2868, 1735, 1715, 1692, 1655, 1620, 1528, 1498, 1455, 1448, 1368, 1365, 1300, 1258, 1188, 1108, 1090, and 1008 cm. The 500 MHz nuclear magnetic resonance spectrum shown in FIG. 3 and the infrared data are consistent with the assigned structure. The molecular formula is $C_{51}H_{71}NO_{15}$.

Figure 4:
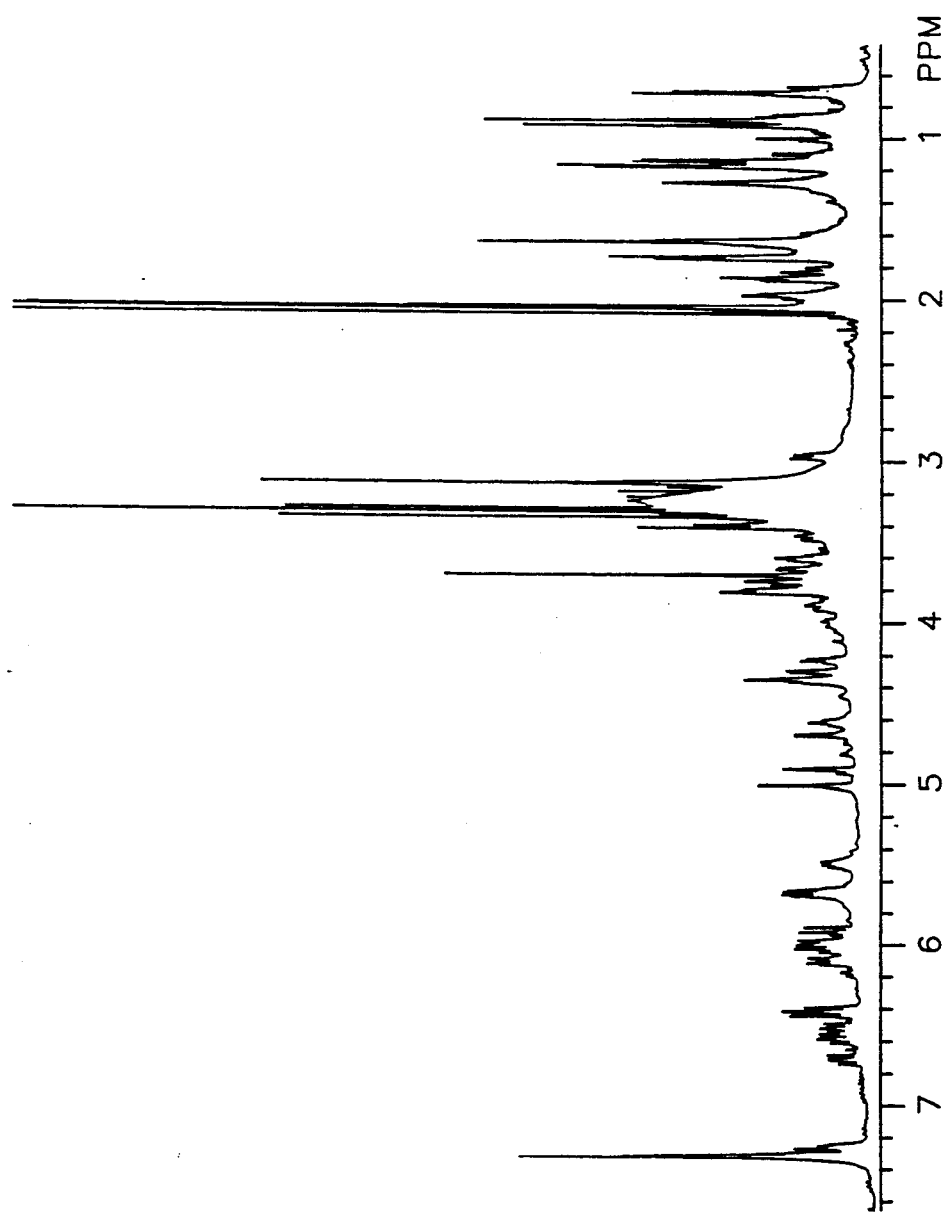
FIG. 4 is a hydrogen nuclear magnetic resonance spectrum of phenelfamycin C at 500 MHz in acetone $d_6$.
Figure 11:
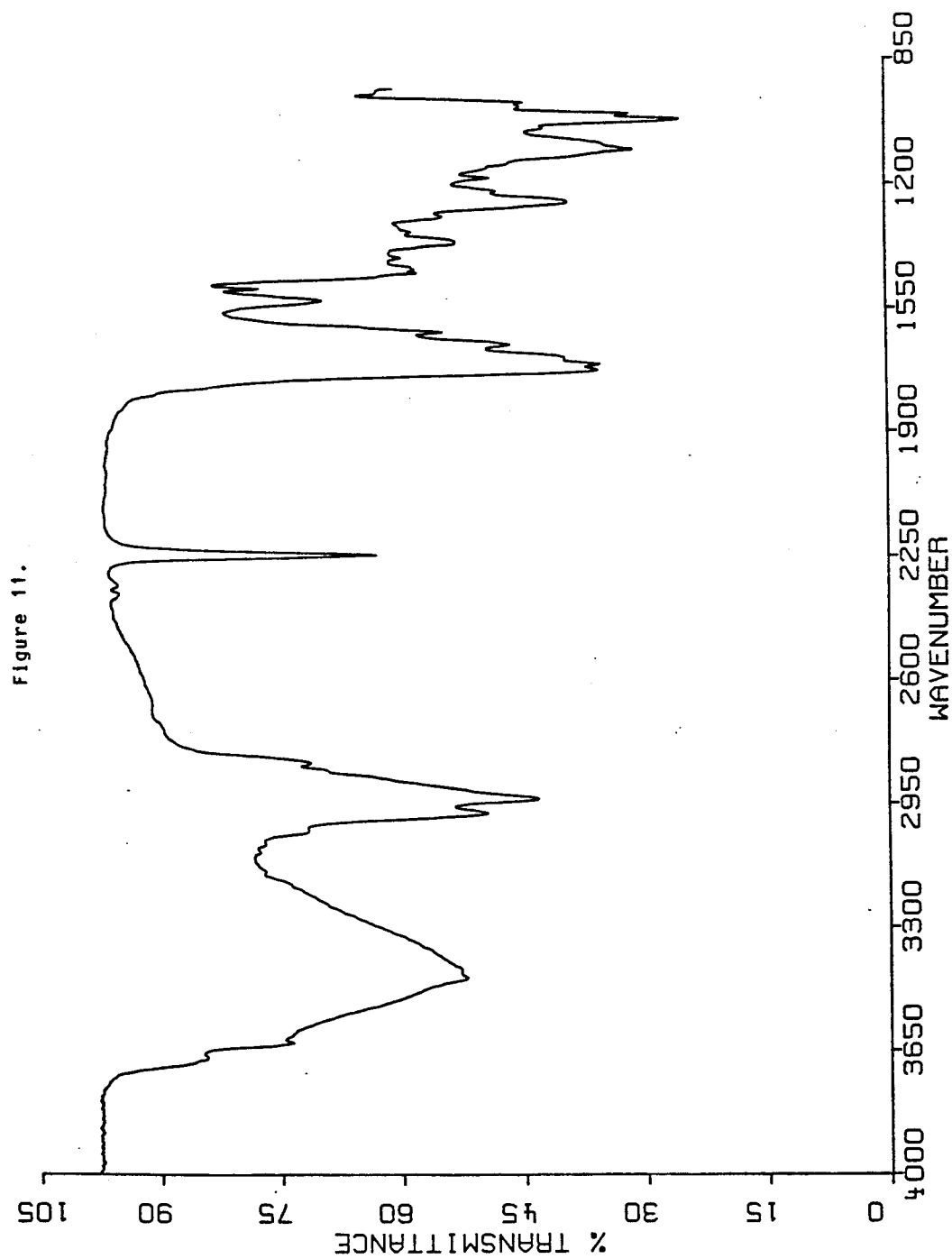
FIG. 11 is an infrared spectrum of phenelfamycin C in $CDCl_3$.

Phenelfamycin C, $[\alpha]_D^{25} = -7.7°$ (c=0.512, MeOH) is a light tan powder with m.p.=88° C. dec. Phenelfamycin C is readily soluble in acetone, methanol, or dimethyl sulfoxide, moderately soluble in chloroform, and insoluble in hexane or water. A molecular weight of 1081 was established for phenelfamycin C by FAB positive ion mass spectrometry. An infrared spectrum measured in CDCl$_3$ (FIG. 11) contained bands at 3445, 3420, 2892, 2868, 1735, 1715, 1692, 1655, 1620, 1528, 1448, 1368, 1365, 1258, 1222, 1188, 1108, 1090, 1008, 990, and 987 cm$^{-1}$. The 500 MHz nuclear magnetic resonance spectrum shown in FIG. 4 and the infrared data are consistent with the assigned structure. The molecular formula is C$_{58}$H$_{83}$HO$_{18}$.

Figure 5:
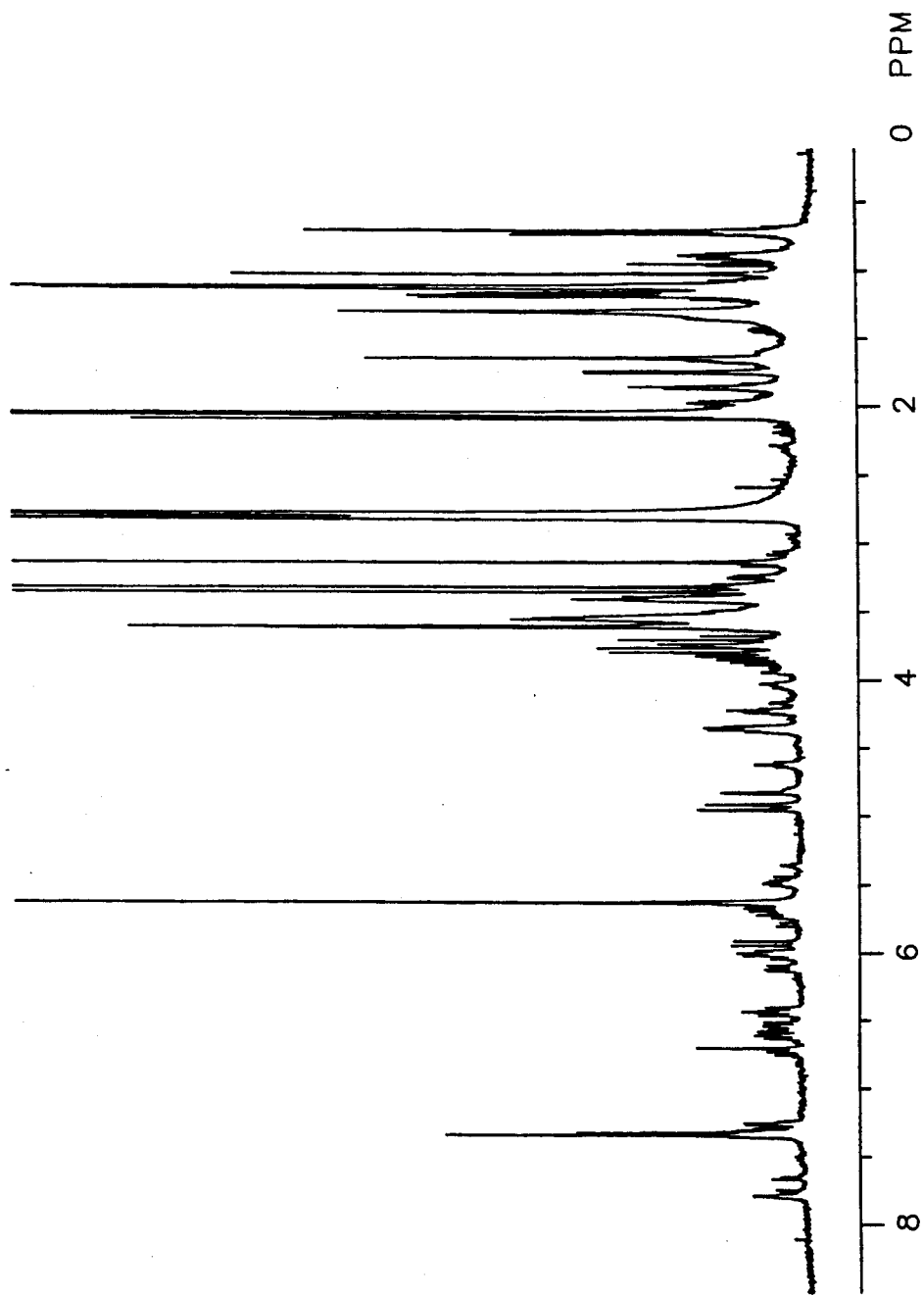
FIG. 5 is a hydrogen nuclear magnetic resonance spectrum of phenelfamycin D at 500 MHz in acetone $d_6$.
Figure 12:
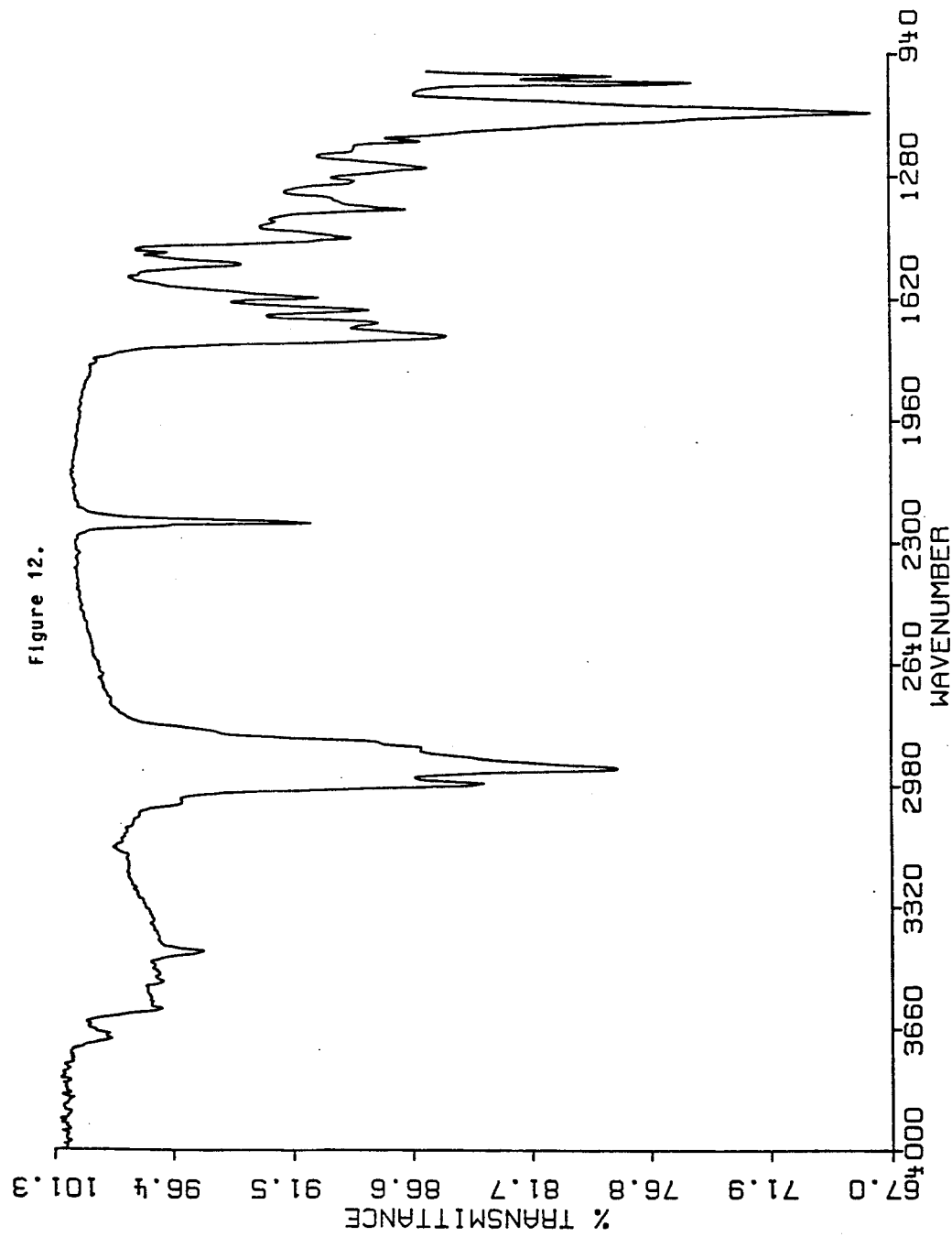
FIG. 12 is an infrared spectrum of phenelfamycin D in $CDCl_3$.

Phenelfamycin D, $[\alpha]_D^{25} = -37°$ (c=0.075, MeOH) is a light tan oil, readily soluble in acetone, methanol, or dimethyl sulfoxide, moderately soluble in chloroform, and insoluble in hexane or water. A molecular weight of 1081 was established for phenelfamycin D by FAB positive ion mass spectrometry. An infrared spectrum measured in CDCl$_3$ (FIG. 12) contained bands at 3445, 2985, 2925, 1725, 1685, 1650, 1615, 1525, 1455, 1378, 1302, 1290, 1256, 1182, 1104, 1024, and 1002 cm$^{-1}$. The 500 MHz nuclear magnetic resonance spectrum shown in FIG. 5 and the infrared data are consistent with the assigned structure. The molecular formula is C$_{58}$H$_{83}$NO$_{18}$.

Figure 6:
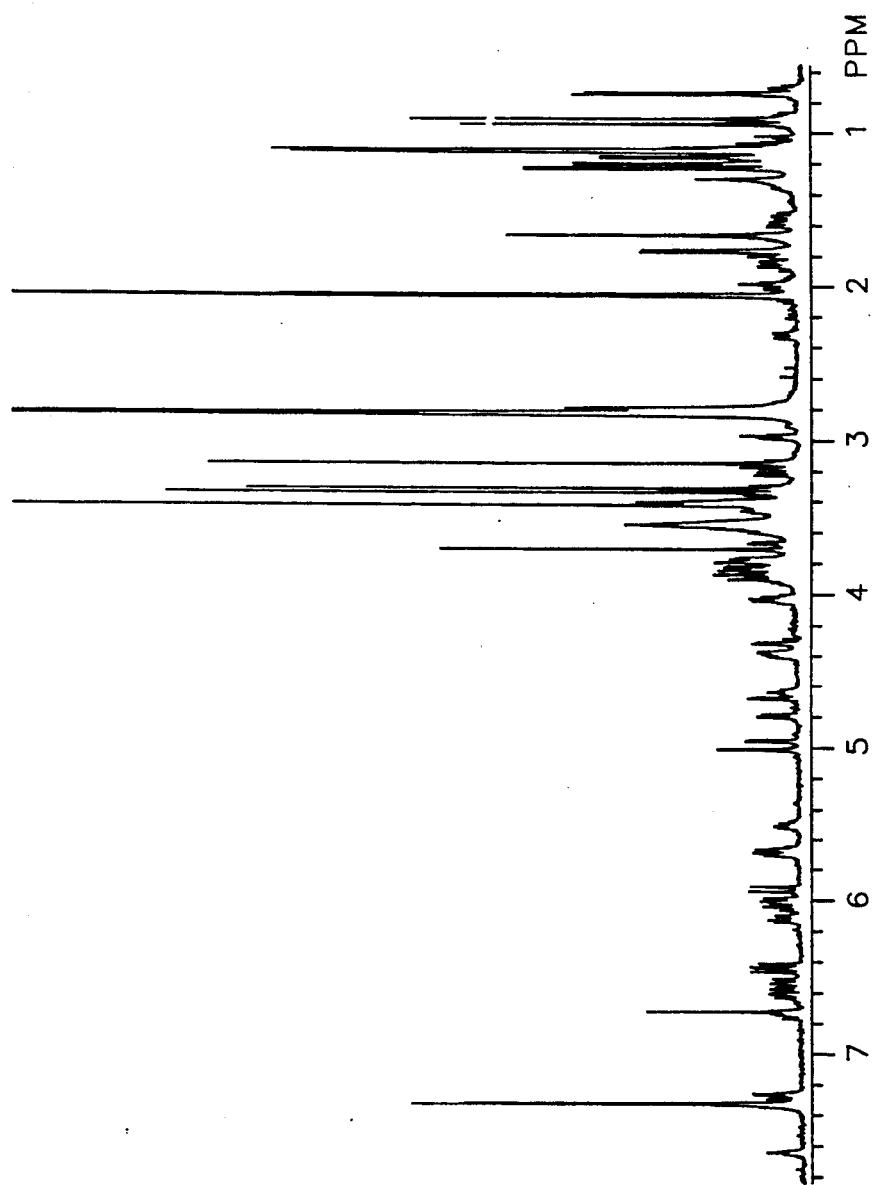
FIG. 6 is a hydrogen nuclear magnetic resonance spectrum of phenelfamycin E at 500 MHz in acetone $d_6$.
Figure 13:
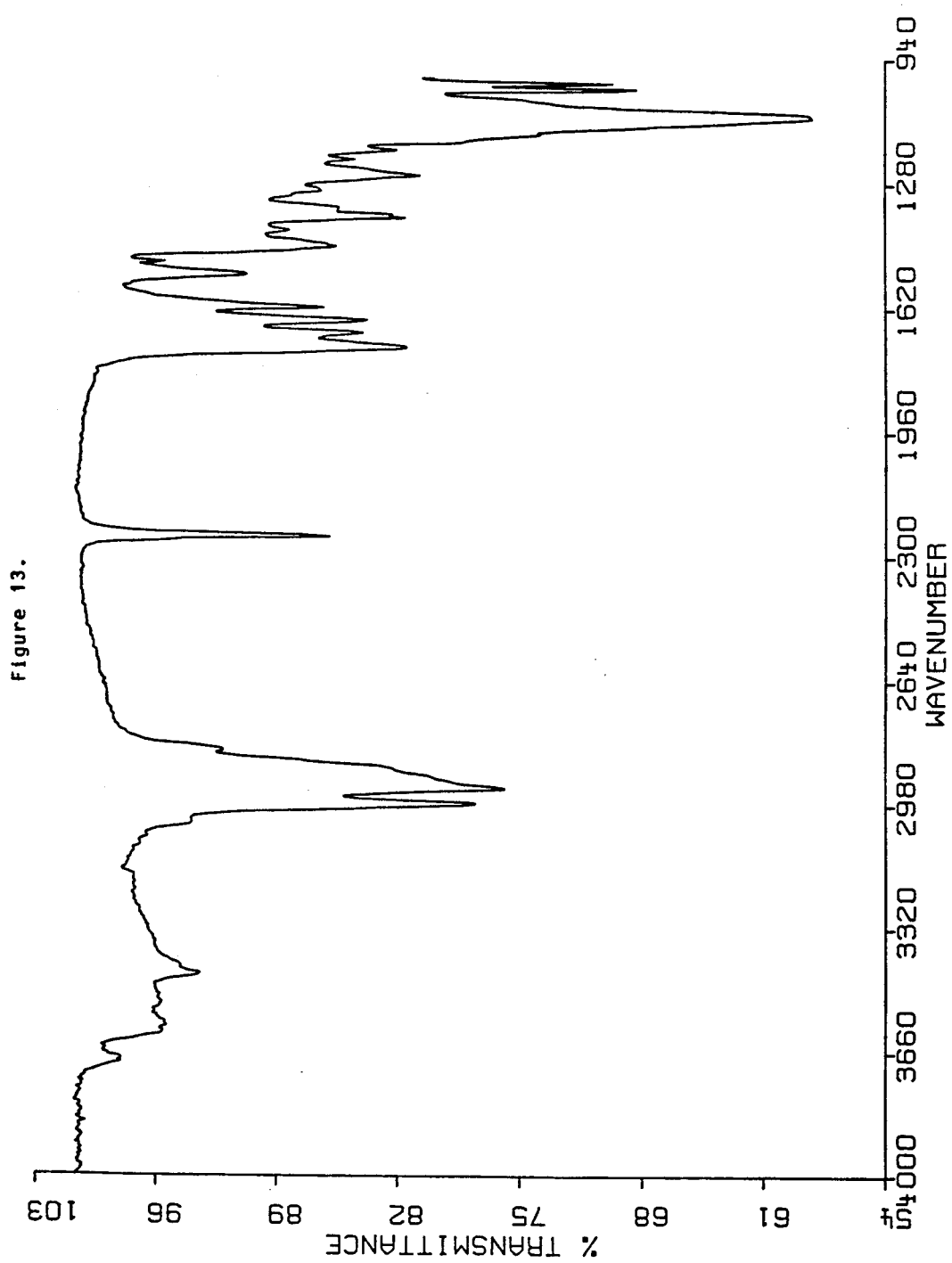
FIG. 13 is an infrared spectrum of phenelfamycin E in $CDCl_3$.

Phenelfamycin E, $[\alpha]_D^{25} = -16.5°$ (c=0.20, MeOH) is a tan powder with m.p.=138° C. dec. Phenelfamycin E is readily soluble in acetone, methanol, or dimethyl sulfoxide, moderately soluble in chloroform, and insoluble in hexane or water. A molecular weight of 1225 was established for phenelfamycin E by FAB positive ion mass spectrometry. An infrared spectrum of phenelfamycin E measured in CDCl$_3$ (FIG. 13) contained bands at 3342, 2984, 2935, 1728, 1682, 1648, 1616, 1524, 1448, 1444, 1376, 1364, 1252, 1216, 1191, 1095, and 1087 cm$^{-1}$. The 500 MHz nuclear magnetic resonance spectrum shown in FIG. 6 and the infrared data are consistent with the assigned structure. The molecular formula is C$_{65}$H$_{95}$NO$_{21}$.

Figure 7:
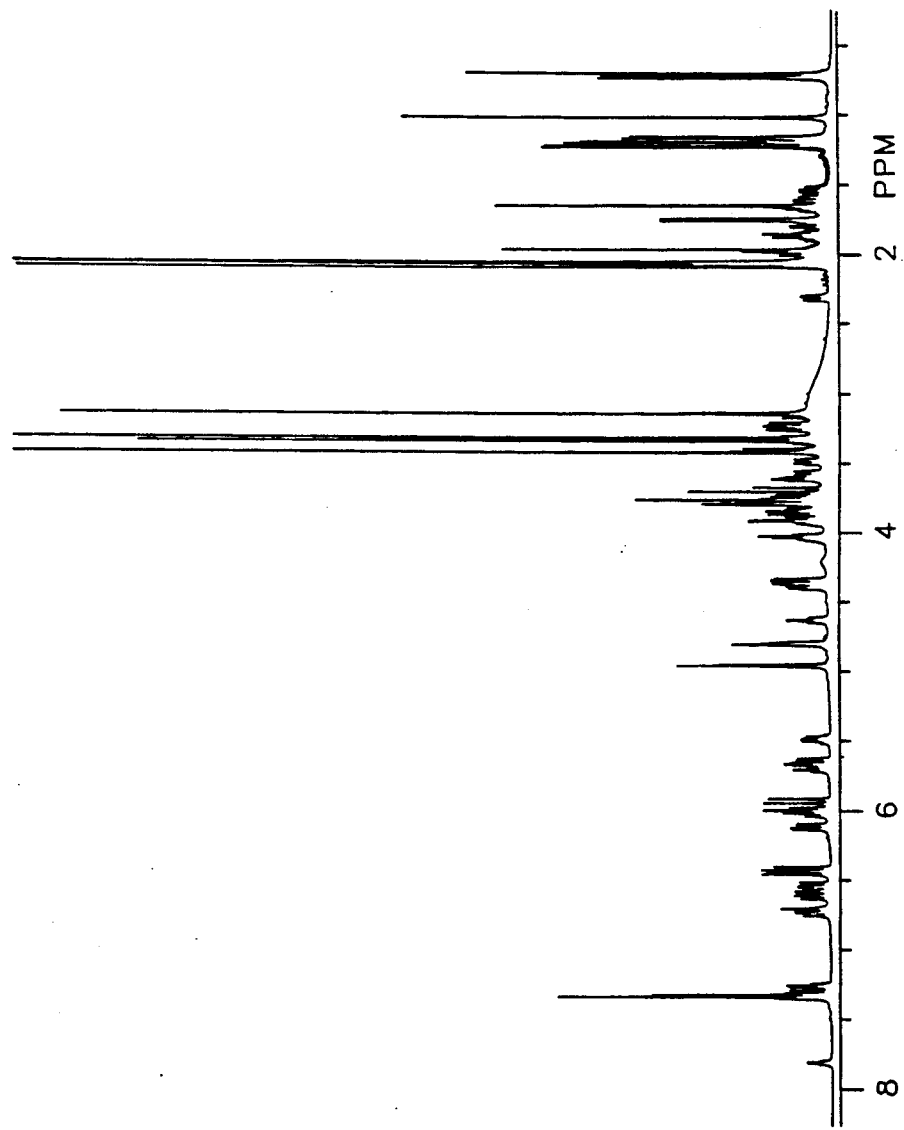
FIG. 7 is a hydrogen nuclear magnetic resonance spectrum of phenelfamycin F at 500 MHz in acetone $d_6$.
Figure 14:
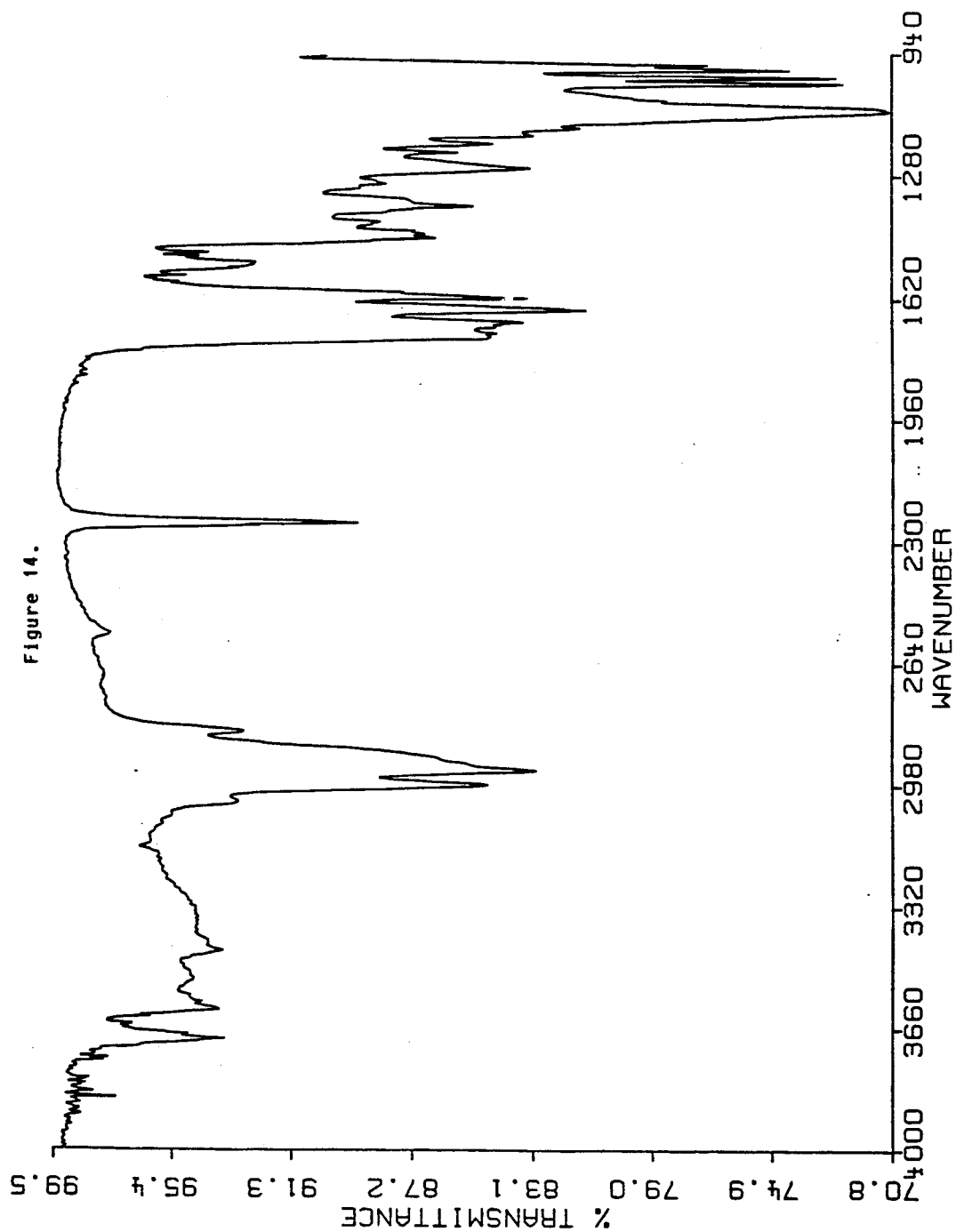
FIG. 14 is an infrared spectrum of phenelfamycin F in $CDCl_3$.

Phenelfamycin F, $[\alpha]_D^{25} = -17°$ (c=1.1, MeOH) is a light tan powder with m.p.=121° C. dec. Phenelfamycin F is readily soluble in acetone, methanol, or dimethyl sulfoxide, moderately soluble in chloroform, and insoluble in hexane or water. A molecular weight of 1225 was established for phenelfamycin F by FAB positive ion mass spectrometry. An infrared spectrum of phenelfamycin F measured in CDCl$_3$ (FIG. 14) contained bands at 3440, 2988, 2936, 1718, 1685, 1653, 1618, 1446, 1367, 1260, 1217, 1192, 1168, 1147, 1099, 1022, 1007, and 972 cm$^{-1}$. The 500 MHz nuclear magnetic resonance spectrum shown in FIG. 7 and the infrared data are consistent with the assigned structure. The molecular formula is C$_{65}$H$_{95}$NO$_{21}$.

The compounds of the present invention also include the pharmaceutically acceptable nontoxic salts of the above phenelfamycins, as for example the alkali and alkaline earth metal salts such as those derived from sodium, calcium, potassium, such as magnesium and ammonium or salts with organic bases such as triethylamine, N-ethylpiperidine or dibenzylethylenediamine.

V. Methods of Use

The antibiotics of the present invention are useful in treating bacterial infections caused by susceptible organisms in humans and other warm-blooded animals. They can be utilized for the treatment of antibiotic-induced colitis, and also as growth permittants for livestock such as poultry, pigs, cattle and sheep.

When used to combat bacterial infections, the total daily dose of the compounds of the invention administered to a host in single or divided doses may be in amounts, for example, of from 0.001 to 100 mg/kg body weight daily and more usually 0.01 to 20 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, rectally, or topically or otherwise in dosage unit formulations containing conventional nontoxic pharmaceutically acceptable carriers, adjuvants, and vehicles as desired. The term "parenteral" as used herein includes subcutaneous injections, intravenous, intramuscular or intrasternal injections, or other infusion techniques.

Injectable preparations, as for example sterile injectable aqueous or oleagenous suspensions, may be formulated according to the known art using suitable dispersing or wetting agents and suspending agents. The sterile injectable preparation may also be a sterile injectable solution or suspension in a nontoxic parenterally acceptable diluent or solvent, such as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at body temperature and will therefore melt in the rectum and release the drug.

Suitable solid dosage forms for oral administration include capsules, tablets, pills, powders, and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

In addition to their use as antibiotics, the compounds of the present invention are useful as feed additive growth promoters or "permittants" for animals such as chickens, sheep, cattle, and pigs. The use of these compounds shortens the time required for bringing animals up to marketable weight and improves feed efficiency, i.e., the amount of weight gain per mass of feed consumed.

agar with $10^{-5}$ CFU (colony forming units) as the inoculum.

TABLE 5

Minimal inhibitroy concentrations (µg/ml) against anaerobic bacteria.

| Organism | Un-phenelfamycin | Phenelfamycin A | Phenelfamycin B | Phenelfamycin C | Phenelfamycin E | Phenelfamycin F |
|---|---|---|---|---|---|---|
| *Bacteroides fragilis* UC-2 | >128 | >128 | >128 | >128 | >128 | >128 |
| *B. thetaiotaomicron* ATCC 29741 | >128 | >128 | >128 | >128 | >128 | >128 |
| *B. melaninogenicus* ATCC 25845 | 128 | >128 | >128 | >128 | 64 | 64 |
| *Fuscobacterium nucleatum* ATCC 25586 | 64 | 128 | 32 | 16 | 64 | 64 |
| *Veillonella parvula* ATCC 10790 | 64 | 64 | 64 | 64 | 32 | 16 |
| *Clostridium perfringens* 788 | 8 | 32 | 64 | 8 | 2 | 1 |
| *C. difficile* ATCC 9689 | 8 | 4 | 4 | 1 | .25 | .25 |
| *C. difficile* ATCC 17857 | 8 | 4 | 4 | 2 | 1 | 1 |
| *Peptopcoccus asaccharolyticus* ATCC 14963 | 16 | .12 | .5 | .5 | .06 | .25 |
| *Peptostreptococcus micros* ATCC 33270 | 2 | .12 | .5 | .12 | .12 | .03 |
| *Propionibacterium acnes* 132 | 4 | 8 | 8 | 16 | 1 | .25 |

When used as growth permittants in animals, the compounds of the invention may be administered as a component of the feed of the animal or may be dissolved or suspended in the drinking water. Typical daily doses when provided in annual feed may be in amounts, for example, of from 0.02 to 10 grams per metric ton of feed or, alternatively, of from 0.0005 to 1.0 mg/kg body weight per day. The compounds may be provided alone or in combination, as for example by the co-administration of phenelfamycins C and D.

When a compound or combination of compounds of the invention is used as a component of animal feed, it is first formulated as a "premix" or feed supplement which in turn is added to the conventional feed. The compound of the invention in the feed supplement is present in relatively concentrated amounts dispersed in an inert carrier or diluent. An inert carrier is one that will not react with the compound of the invention and one that may be administered safely to animals. Typical carriers or diluents acceptable for such compositions include, for example, corn meal, citrus meal, fermentation residues, ground oyster shells, wheat shorts, molasses solubles, corn cob meal, edible bean mill feed, soya grits, crushed limestone and the like. The compound of the invention is dispersed throughout the carrier by methods such as grinding, stirring, milling, or tumbling. Premix compositions containing from about 0.5 to 25% by weight of a compound of the invention are particularly suitable as feed supplements.

An alternative method of administration is to dissolve or suspend a compound of the invention in the drinking water of the animals. Emulsifiers or surfaceactive agents may be used to increase the amount of the compound that may be suspended in the water without undue settling.

Animal feeds containing a compound of the invention may also include vitamins, other antibiotics and growth-promoting agents and other nutritional substances.

VI. Antimicrobial Activity

The antimicrobial activities of phenelfamycins A-F and unphenelfamycin were tested against a variety of anaerobic bacteria, and are illustrated in Table 5 below. Minimum inhibitory concentrations were determined by the agar dilution method using Wilkins-Chalgren It is evident from the above results that phenelfamycins A-F and unphenelfamycin have activity against gram-positive and gram-negative anaerobic bacteria.

VII. Growth Permittant Activity

The growth permittant effect of phenelfamycins A-F on broiler chickens were tested in two studies, the results of which are shown below in Tables 6 and 7. In the first study, 840 twelve-day-old Arbor Acre X Arbor Acre male broiler chicks were separated into 14 groups of 60 chicks each, 12 birds per pen. Conventional broiler diet and water were provided ad libidum, with all feed containing the coccidiostat salinomycin (BIOCOX brand) at 60 grams per metric ton.

Phenelfamycins A-F were each formulated as a premix of soy mill feed and soybean oil containing approximately 2% by weight of the test compound. Feeds for the various test groups were then supplemented with the premix to produce the doses shown in Table 6. A positive control group was given feed containing the growth permittant bacitracin, while a negative control group was given feed containing no supplement. The birds were grown as described until Day 40, with feed consumption being recorded for each pen, and were then weighed to obtain the results shown.

In the second study, 4320 newly hatched Arbor Acre X Arbor Acre straight-run broiler chicks were divided into 9 groups of 480 chicks each, 60 birds per pen. Medicated feed and water were provided as in the previous study, and control groups were established as before. Two phenelfamycin premixes were prepared containing phenelfamycin pairs A and B ("A+B") and C and D ("C+D"), and were used to supplement the feed at the dose rates shown. (Subsequent analysis by HPLC showed the A+B mixture to consist of 51.3 and 43.4% phenelfamycins A and B, respectively, while the C+D mixture contained 24.0 and 60.1% phenelfamycins D and D, respectively; these figures were obtained using the area percent method and a UV detection system at 298 nm wavelength.)

Seven of the test groups were fed diet supplemented with the above mixtures at the dose rates shown. After 46 days, data for the nine groups of birds were collected and processed to obtain the results shown in Table 7.

TABLE 6
Weight Gain and Feed Efficiency Improvement in Broiler Chickens

| Group | Dose (g/Ton) | Final Wt. (kg) | Feed/Gain | % Inc. vs. Control Gain | % Inc. vs. Control Feed/Gain |
|---|---|---|---|---|---|
| Control | — | 1.532 | 2.044 | — | — |
| BMD* | 50 | 1.568 | 1.916 | 3.8 | 6.3 |
| Phen A | 0.16 | 1.468 | 1.940 | −3.0 | 5.1 |
|  | 0.80 | 1.604 | 1.932 | 5.8 | 5.5 |
| Phen B | 0.19 | 1.572 | 1.912 | 3.8 | 6.5 |
|  | 0.93 | 1.574 | 1.902 | 3.8 | 6.9 |
| Phen C | 0.23 | 1.557 | 1.916 | 2.7 | 6.3 |
|  | 1.13 | 1.580 | 1.912 | 3.1 | 6.5 |
| Phen D | 0.18 | 1.636 | 1.918 | 7.5 | 6.2 |
|  | 0.91 | 1.593 | 1.925 | 3.9 | 5.8 |
| Phen E | 0.38 | 1.570 | 1.924 | 3.5 | 5.9 |
|  | 1.92 | 1.620 | 1.940 | 4.8 | 5.1 |
| Phen F | 0.41 | 1.592 | 1.873 | 5.0 | 8.4 |
|  | 2.04 | 1.572 | 1.869 | 3.1 | 8.6 |

*Note:
BMD = bacitracin methylene disalycilate

TABLE 7
Weight Gain and Feed Efficiency Improvement in Broiler Chickens

| Group | Dose (g/Ton) | Final Wt. (kg) | Feed/Gain | % Inc. vs. Control Gain | % Inc. vs. Control Feed/Gain |
|---|---|---|---|---|---|
| Control | — | 1.733 | 2.018 | — | — |
| BMD* | 50 | 1.773 | 2.000 | 2.4 | 0.9 |
| Phen A + B | 0.1 | 1.791 | 1.955 | 3.3 | 2.6 |
|  | 0.25 | 1.800 | 1.929 | 3.9 | 4.6 |
|  | 1.0 | 1.779 | 1.970 | 2.6 | 2.4 |
|  | 2.5 | 1.783 | 1.965 | 2.9 | 2.7 |
| Phen C + D | 0.1 | 1.756 | 1.955 | 1.3 | 3.2 |
|  | 0.25 | 1.801 | 1.917 | 3.9 | 5.0 |
|  | 1.0 | 1.758 | 1.971 | 1.4 | 2.3 |

*Note:
BMD = bacitracin methylene disalycilate

These results demonstrates that the compounds of the present invention are active in promoting growth rate and feed efficiency.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed:

1. A compound of the formula:

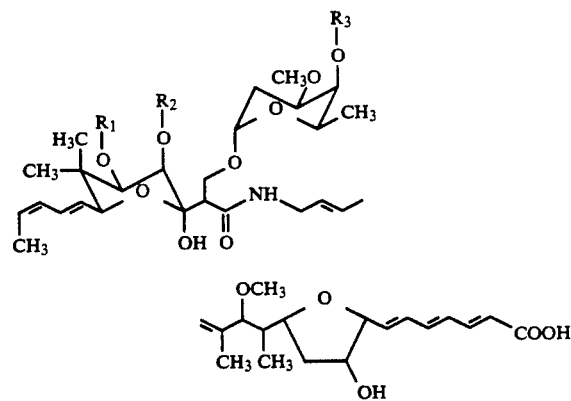

or a pharmaceutically acceptable salt thereof, wherein $R_1$ and $R_2$ are independently selected from the group consisting of hydrogen and $-C(O)CH_2C_6H_5$, with the proviso that at least one of $R_2$ and $R_2$ is hydrogen, and $R_3$ is selected from the group consisting of hydrogen and

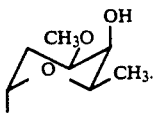

2. A composition having antibacterial activity which comprises a pharmaceutically acceptable carrier and a therapeutically effective amount of a compound of the formula:

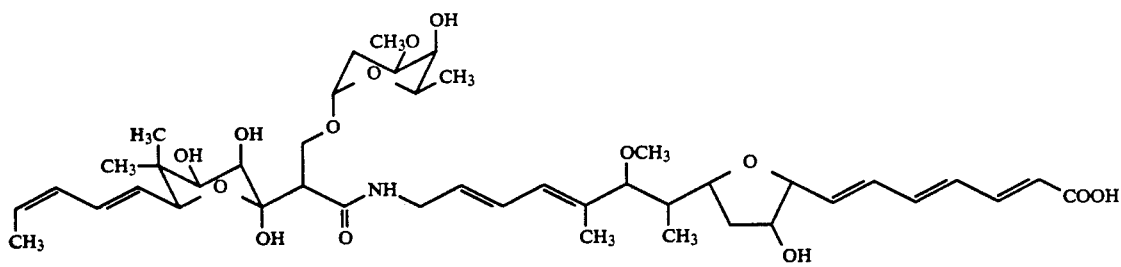

or a pharmaceutically acceptable salt thereof.

3. A composition having antibacterial activity which comprises a pharmaceutically acceptable carrier and a therapeutically effective amount of a compound of the formula:

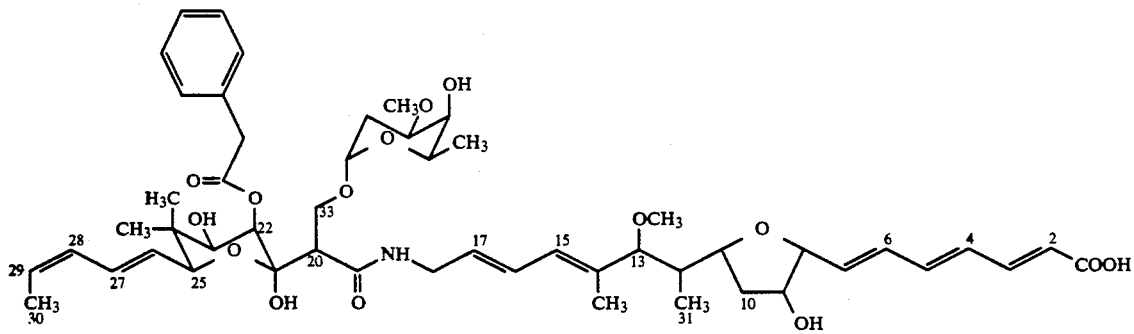

or a pharmaceutically acceptable salt thereof.

4. A composition having antibacterial activity which comprises a pharmaceutically acceptable carrier and a therapeutically effective amount of a compound of the formula:

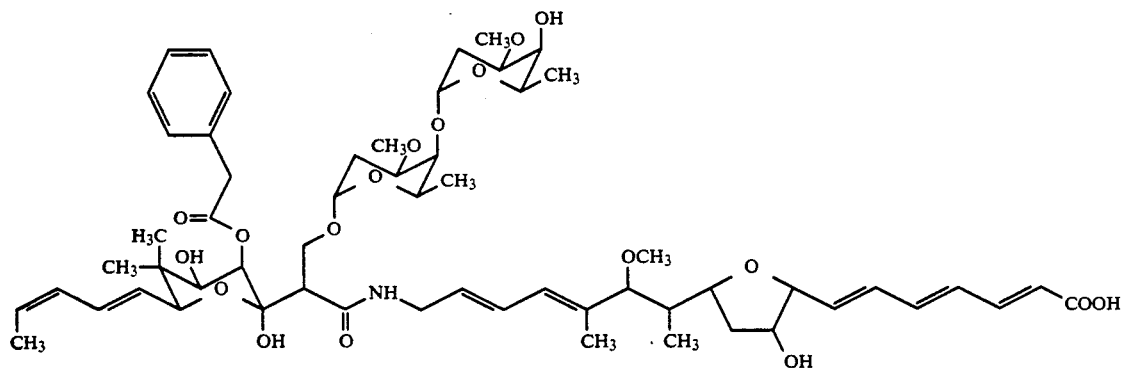

or a pharmaceutically acceptable salt thereof.

5. A composition having antibacterial activity which comprises a pharmaceutically acceptable carrier and a therapeutically effective amount of a compound of the formula:

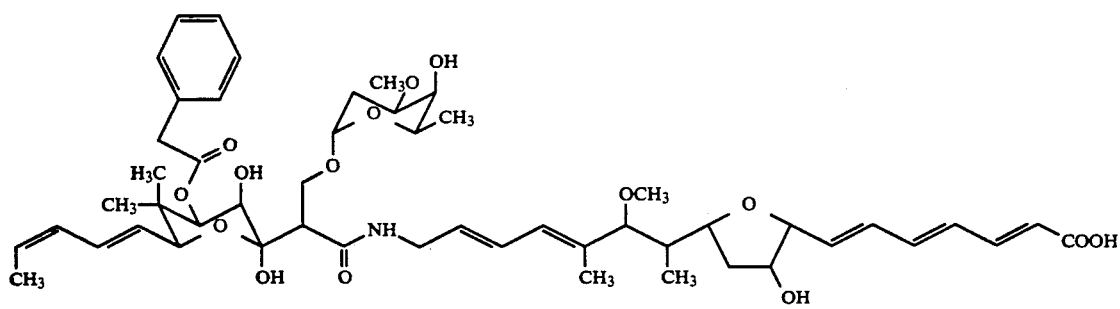

or a pharmaceutically acceptable salt thereof.

6. A composition having antibacterial activity which comprises a pharmaceutically acceptable carrier and a therapeutically effective amount of a compound of the formula:

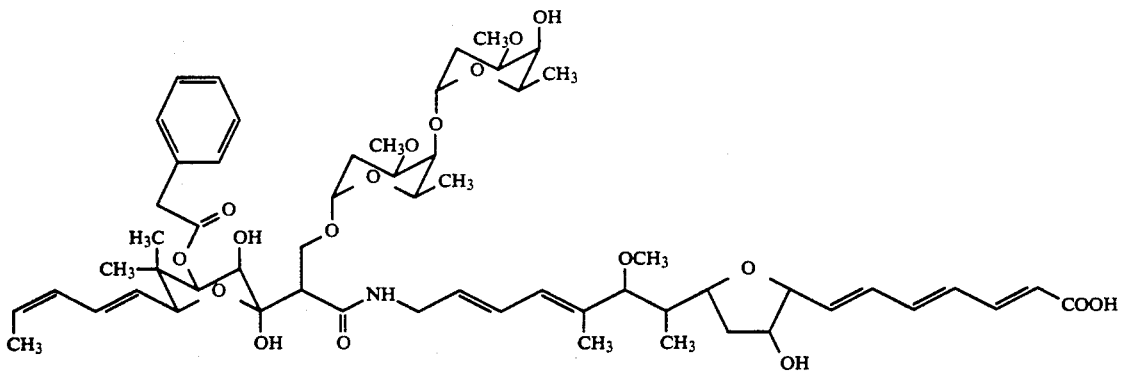

or a pharmaceutically acceptable salt thereof.

7. A method of treating a gram-positive or gram-negative bacterial infection in a human or animal comprising administering to a human or animal in need of such treatment a therapeutically effective amount of a compound of claim 1.

8. A method of increasing the growth rate and feed efficiency of animals comprising administering to said animals an effective amount of a compound of claim 1.

9. The method of claim 8 wherein the animals are selected from the group consisting of poultry, sheep, cattle and swine.

10. The method of claim 9 wherein the animals are chickens.

11. The method of claim 8 wherein the compound is administered orally in an amount of between about 0.0005 and about 1.0 mg/kg body weight per day.

12. The method of claim 8 wherein the compound is administered with animal feed at a dose rate of between 0.02 and 10 grams per metric ton of feed.

* * * * *